United States Patent
Turcott

(10) Patent No.: US 7,881,790 B1
(45) Date of Patent: *Feb. 1, 2011

(54) REDUCING DATA ACQUISITION, POWER AND PROCESSING FOR PHOTOPLETHYSMOGRAPHY AND OTHER APPLICATIONS

(75) Inventor: Robert G. Turcott, Mountain View, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 271 days.

This patent is subject to a terminal disclaimer.

(21) Appl. No.: 11/948,231

(22) Filed: Nov. 30, 2007

Related U.S. Application Data

(62) Division of application No. 10/897,336, filed on Jul. 21, 2004, now Pat. No. 7,324,848.

(51) Int. Cl.
*A61N 1/365* (2006.01)
(52) U.S. Cl. .................. 607/17; 607/6; 607/20
(58) Field of Classification Search ........ 600/483, 600/513, 529; 607/6, 17, 20
See application file for complete search history.

(56) References Cited

U.S. PATENT DOCUMENTS

| | | | |
|---|---|---|---|
| 3,939,824 A | 2/1976 | Arneson et al. | |
| 4,036,217 A | 7/1977 | Ito et al. | |
| 4,137,907 A | 2/1979 | Jansen | |
| 4,190,886 A | 2/1980 | Sherman | |
| 4,223,681 A | 9/1980 | Sherman | |
| 4,305,398 A | 12/1981 | Sawa | |
| 4,461,266 A | 7/1984 | Hood, Jr. et al. | |
| 4,505,276 A | 3/1985 | Markowitz et al. | |
| 4,562,843 A * | 1/1986 | Djordjevich et al. | 600/485 |
| 4,700,708 A | 10/1987 | New, Jr. et al. | |
| 4,759,369 A | 7/1988 | Taylor | |
| 4,815,469 A | 3/1989 | Cohen | |
| 4,869,254 A | 9/1989 | Stone | |
| 4,919,144 A | 4/1990 | Vandehey | |
| 5,078,136 A | 1/1992 | Stone | |
| 5,129,392 A | 7/1992 | Bardy | |
| 5,241,964 A | 9/1993 | McQuilkin | |
| 5,309,916 A | 5/1994 | Hatschek | |
| 5,343,868 A | 9/1994 | Kurscheidt | |
| 5,533,511 A | 7/1996 | Kaspari et al. | |
| 5,743,267 A * | 4/1998 | Nikolic et al. | 600/483 |
| 5,797,399 A | 8/1998 | Morris | |
| 5,957,861 A | 9/1999 | Combs | |

(Continued)

FOREIGN PATENT DOCUMENTS

EP          1302156 A2    4/2003

(Continued)

OTHER PUBLICATIONS

Non-Final Office Action mailed Feb. 25, 2008: Related U.S. Appl. No. 10/894,962.

(Continued)

*Primary Examiner*—Carl H Layno
*Assistant Examiner*—Jennifer Stewart
(74) *Attorney, Agent, or Firm*—Steven M. Mitchell

(57) ABSTRACT

Hemodynamic signals, such as photoplethysmography (PPG) signals, pressure signals, and impedance signals, are sampled once per cyclical body cycle to reduce the amount of data, processing and/or power required to analyze the hemodynamic signals.

18 Claims, 16 Drawing Sheets

U.S. PATENT DOCUMENTS

| | | | |
|---|---|---|---|
| 6,122,536 | A | 9/2000 | Sun |
| 6,409,675 | B1 | 6/2002 | Turcott |
| 6,449,509 | B1 * | 9/2002 | Park et al. ............... 607/20 |
| 6,480,733 | B1 | 11/2002 | Turcott |
| 6,519,486 | B1 | 2/2003 | Edgar, Jr. et al. |
| 6,561,984 | B1 | 5/2003 | Turcott |
| 6,575,912 | B1 | 6/2003 | Turcott |
| 6,591,131 | B2 | 7/2003 | Dal-Molin |
| 7,092,759 | B2 | 8/2006 | Nehls |
| 2001/0034488 | A1 | 10/2001 | Policker |
| 2004/0042581 | A1 | 3/2004 | Okerlund |
| 2004/0077953 | A1 | 4/2004 | Turcott |
| 2004/0254483 | A1 | 12/2004 | Zdeblick |
| 2005/0137487 | A1 | 6/2005 | Zhu et al. |

FOREIGN PATENT DOCUMENTS

| | | |
|---|---|---|
| WO | 9701986 | 1/1997 |

OTHER PUBLICATIONS

Non-Final Office Action mailed Sep. 16, 2008: Related U.S. Appl. No. 10/894,962.

Final Office Action mailed Aug. 4, 2009: Related U.S. Appl. No. 10/894,962.

Non-Final Office Action mailed Oct. 16, 2006: Related U.S. Appl. No. 10/895,004.

Non-Final Office Action mailed May 4, 2007: Related U.S. Appl. No. 10/897,336.

Notice of Allowance mailed May 4, 2007: Related U.S. Appl. No. 10/897,336.

Non-Final Office Action mailed Jan. 10, 2006: Related U.S. Appl. No. 10/895,165.

Final Office Action mailed May 25, 2006: Related U.S. Appl. No. 10/895,165.

Advisory Action mailed Aug. 2, 2006: Related U.S. Appl. No. 10/895,165.

Non-Final Office Action mailed Sep. 29, 2006: Related U.S. Appl. No. 10/895,165.

* cited by examiner

| Red-to-Infrared Ratio | O2 Saturation Level |
|---|---|
| Ratio_1 | O2_Sat_1 |
| Ratio_2 | O2_Set_2 |
| Ratio_3 | O2_Sat_3 |
| . | . |
| . | . |
| . | . |
| Ratio_n | O2_Sat_n |

FIG. 11A

| | Infrared_1 | Infrared_2 | Infrared_3 | . . . | Infrared_m |
|---|---|---|---|---|---|
| Red_1 | O2_Sat_1,1 | O2_Sat_1,2 | O2_Sat_1,3 | . . . | O2_Sat_1,m |
| Red_2 | O2_Sat_2,1 | O2_Sat_2,2 | O2_Sat_2,3 | . . . | O2_Sat_2,m |
| Red_3 | O2_Sat_3,1 | O2_Sat_3,2 | O2_Sat_3,3 | . . . | O2_Sat_3,m |
| . | . | . | . | . . . | . |
| . | . | . | . | . . . | . |
| . | . | . | . | . . . | . |
| Red_n | O2_Sat_n,1 | . | . | . . . | O2_Sat_m,n |

FIG. 11B

REDUCING DATA ACQUISITION, POWER AND PROCESSING FOR PHOTOPLETHYSMOGRAPHY AND OTHER APPLICATIONS

PRIORITY CLAIM

This application is a Divisional of U.S. patent application Ser. No. 10/897,336, filed Jul. 21, 2004, now U.S. Pat. No. 7,324,848, which is incorporated herein by reference.

FIELD OF THE INVENTION

Embodiments of the present invention relate to reducing the amount of data, processing and/or power required to analyze hemodynamic signals such as photoplethysmography signals and arterial pressure signals.

RELATED APPLICATIONS

The present application is related to the following commonly invented and commonly assigned patent applications, each of which was filed on the same day as the present application, and each of which is incorporated herein by reference:

U.S. patent application Ser. No. 10/895,165 entitled "Reducing Data Acquisition, Power and Processing for Hemodynamic Signal Amplitude Detection";

U.S. patent application Ser. No. 10/894,962 entitled "Reducing Data Acquisition, Power and Processing for Hemodynamic Signal Sampling"; and U.S. patent application Ser. No. 11/734,861 which is a division of U.S. patent application Ser. No. 10/895,004, now abandoned, entitled "Reducing Data Acquisition, Power and Processing for Pulse Oximetry Applications".

FIELD OF THE INVENTION

Background of the Invention

FIG. 1 illustrates an exemplary photoplethysmography (PPG) signal 102 produced using a PPG device (also known as a PPG sensor). For timing reference, an electrocardiogram (ECG) signal 104 is also illustrated. The PPG signal 102 can be used to measure the volume of arterial and venous vasculature. Additionally, a measure of arterial pulse amplitude can be derived from the PPG signal 102. A few tens to a few hundreds of milliseconds after the QRS complex of the ECG signal 104, the PPG waveform reaches a minimum and starts to increase. This is due to the increasing blood volume in the arterioles as the systolic pulse reaches the periphery. The delay is influenced by the distance that the PPG sensor is placed from the heart. It requires approximately 100 msec for the waveform to reach its maximum. The excursion from minimum to maximum represents the arterial pulse amplitude. During diastole, the recoil of the elastic arterial vessels continues to force blood through the capillaries, so that blood flows through the capillary bed throughout the entire cardiac cycle.

A PPG sensor (also called a pseudoplethysmography or photoelectric plethysmography sensor) includes a light source and a light detector. The PPG sensor utilizes the transmission or reflection of light to demonstrate the changes in blood perfusion. Such devices might be used, e.g., in the cardiology department or intensive care department of a hospital or in a clinic for diagnostic purposes related to vascular surgery.

A block diagram of an exemplary PPG sensor is shown in FIG. 2A. An exemplary mechanical arrangement for a non-invasive (i.e., not implanted) PPG sensor is shown in FIG. 2B. An exemplary mechanical arrangement for a chronically implantable PPG sensor is shown in FIG. 2C.

The PPG sensor includes a light source 206 and a light detector 214. In one example, the light source 206 includes one or more light-emitting diode (LED), although in alternative models an incandescent lamp or laser diode can be used as the light source. Referring to FIG. 2A, the light source 206 outputs a transmit light signal 208 that is transmitted through and/or reflected by (depending on the embodiment) patient tissue 210. For example, light may be transmitted through a capillary bed such as in an earlobe or finger tip. As arterial pulsations fill the capillary bed and pre-capillary arterioles, the changes in volume of the blood vessels modify the absorption, reflection and scattering of the light. Stated another way, an arterial pulse in, for example, a finger tip, or earlobe, causes blood volume to change, thereby changing the optical density of the tissue. Therefore, the arterial pulse modulates the intensity of the light passing through the tissue.

A receive light signal 212 is received by the light detector 214. The light detector 214 can include, for example, a photodiode. Changes in light intensity cause proportional changes in the photodiode current, which can be converted to a varying analog voltage light detection signal 216 by a transimpedance amplifier. The light detector can, for example, alternatively include a photoresistor, phototransistor, photodarlington or avalanche photodiode. Light detectors are often also referred to as photodetectors or photocells.

PPG sensors may operate in either a transmission configuration or a reflection configuration. In the transmission configuration, the light source 206 and the light detector 214 face one another and a segment of the body (e.g., a finger or earlobe) is interposed between the source 206 and the detector 214. In the reflection configuration, the light source 206 and the light detector 214 are mounted adjacent to one another, e.g., on the surface of the body, as shown in FIG. 2B. In this configuration, a fraction of light from the light source 206 is backscattered by the tissue into the light detector 214.

Referring to FIG. 2C, if the PPG sensor is incorporated into a chronically implantable device 220 (e.g., an implantable cardioverter defibrillator (ICD), pacemaker, or any other implantable device), the light source 206 and the light detector 214 can be mounted adjacent to one another on the housing or header of the implantable device. The light source 206 and the light detector 214 are preferably placed on the side of the implantable device 220 that, following implantation, faces the chest wall, and are configured such that light cannot pass directly from the source to the detector. Thus, the reflection configuration is preferably used when the plethysmography device is implemented in an implantable device. The placement on the side of the device 220 that faces the chest wall maximizes the signal to noise ratio by 1) directing the signal toward the highly vascularized musculature, and 2) shielding the source and detector from ambient light that enters the body through the skin. Alternatively, at the risk of increasing susceptibility to ambient light, the light source 206 and the light detector 214 can be placed on the face of the device that faces the skin of the patient. Additional details of an implantable PPG device are disclosed in U.S. Pat. No. 6,491,639, entitled "Extravascular Hemodynamic Sensor" (Turcott), which is incorporated herein by reference.

The varying analog voltage light detection signal 216 that is produced by the light detector 214 is a PPG signal. The PPG signal is typically filtered, amplified and converted to a digital signal using an analog to digital (A/D) converter (not necessarily in the order). For example, the signal may be sampled at 500 Hz (i.e., 500 samples per second) using a high resolution A/D converter, and then the samples may undergo relatively intensive post-acquisition filtering (e.g., using a 1000-point digital filter). This relatively high sampling rate and relatively intensive filtering consume battery power and processing resources. While this may not be much of a concern with a non-implanted PPG device (e.g., such as the one shown in FIG. 2B), minimizing power consumption and processing is very important when it comes to implantable devices. This is in part because invasive surgery is required to replace the battery of an implanted device.

Accordingly, there is a desire to reduce, and hopefully minimize, both the number of samples that are acquired, and the associated processing of such samples. Additionally, there is a desire to reduce the amount of power that is required to produce and process the samples.

SUMMARY OF THE INVENTION

Embodiments of the present invention relate to methods, and systems (which can be implemented as devices) for reducing the amount of data, processing and/or power required to analyze hemodynamic signals such as photoplethysmography signals and arterial pressure signals.

In accordance with embodiments of the present invention, for a window of time that spans at least two cycles of a cyclical body function (e.g., heart beat or respiration), only one sample of a hemodynamic signal is produced per cycle (e.g., cardiac cycle or respiratory cycle), at a substantially same instant in each cycle. This results in a plurality of samples being produced for the window. The hemodynamic signal is then analyzed based on the plurality of samples.

In accordance with embodiments of the present invention, for each of a plurality of windows of time, only one sample of a hemodynamic signal is produced per cycle of a cyclical body function, at a substantially same instant in each cycle. This results in a plurality of samples being produced for each window, wherein each window spans at least two cycles of the cyclical body function. The plurality of samples for each window can then be averaged, to thereby produce an average value for each window. The hemodynamic signal is then analyzed based on the averages values.

In accordance with further embodiments of the present invention, in response to detecting a specific event associated with a cyclical body function, analog circuitry is used to detect and store a minimum and a maximum of the hemodynamic signal within a window of time. For example, a first analog peak detector is used to detect and store the maximum, and a second analog peak detector is used to detect and store the minimum. The stored minimum and the stored maximum are then sampled to produce a pair of samples from which the peak-to-peak amplitude can be determined.

In accordance with other embodiments of the present invention, in response to detecting a specific event associated with a cyclical body function, a hemodynamic signal is continuously sampled during a window following the detecting of the specific event, wherein the window is shorter than a cycle associated with the cyclical body function. The continuous sampling may be at about 20 Hz or greater if the cyclical body function is heart beat, or at about 1 Hz or greater if the cyclical body function is respiration. This results is a plurality of samples being produced for the window. The hemodynamic signal is then analyzed based on the plurality of samples.

Embodiments of the present invention also relate to reducing the amount of processing required to determine blood oxygen ($O_2$) saturation levels.

In accordance with embodiments of the present invention, a measure of DC offset and pulse amplitude associated with a received first light signal (e.g., a red light signal) are obtained, and a normalized first light pulse amplitude is produced therefrom. Similarly, a measure of DC offset and pulse amplitude associated with a received second light signal (e.g., an infrared or near infrared light signal) is obtained, and a normalized second light pulse amplitude is produced therefrom. Then, a two dimensional look-up table is used to determine an O2 saturation level based on the normalized first light pulse amplitude and the normalized second light pulse amplitude.

In accordance with embodiments of the present invention, light of a first wavelength and light of a second wavelength are transmitted from a light source to a light detector (e.g., of a pulse oximetry device), such that a corresponding DC offset and pulse amplitude can be determined for light of the first wavelength received at the light detector and a corresponding DC offset and pulse amplitude can be determined for light of the second wavelength received at the light detector. An intensity of the transmitted light of the first wavelength is adjusted so that the DC offset for the light of the first wavelength received at the light detector is maintained at a substantially constant predetermined level. Similarly, the intensity of the transmitted light of the second wavelength is adjusted so that the DC offset for the light of the second wavelength received at the light detector is maintained at a substantially constant predetermined level. This enables an O2 saturation level to be determined based on a pulse amplitude determined for the light of the first wavelength received at the light detector and a pulse amplitude determined for the light of the second wavelength received at the light detector, without having to normalize the pulse amplitudes.

In accordance with an embodiment of the present invention, prior to high pass filtering, a first light signal and a second light signal are sampled to determine an estimate of each signal's DC offset. The first light signal is indicative of light of a first wavelength that is received at the light detector, and the second light signal is indicative of light of a second wavelength that is received at the light detector. Then, after high pass filtering, the first light signal and the second light signal are sampled to determine a pulse amplitude for each signal, wherein the sampling before high pass filtering is at a lower frequency than the sampling after high pass sampling, to thereby reduce the amount of data produced. Then, an O2 saturation level is determined based on the estimates of DC offset for the first and second light signals and the pulse amplitudes for the first and second light signals.

Other features and advantages of the invention will appear from the following description in which the preferred embodiments have been set forth in detail, in conjunction with the accompanying drawings and claims.

BRIEF DESCRIPTION OF THE FIGURES

FIG. 11A illustrates an exemplary one dimensional look-up table that could be used for determining oxygen saturation levels.

FIG. 11B illustrates an exemplary two dimensional look-up table, according to an embodiment of the present invention, that could be used for determining oxygen saturation levels.

DETAILED DESCRIPTION OF THE INVENTION

Exemplary Photoplethysmography Sensors

Figure 2A:
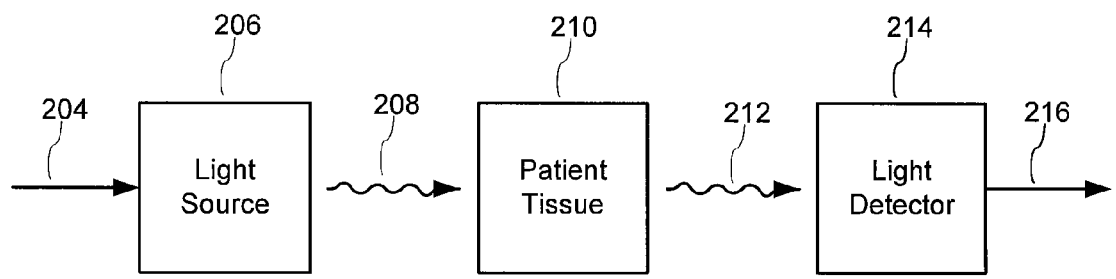
FIG. 2A is a high level block diagram of an exemplary PPG sensor.
Figure 3A:
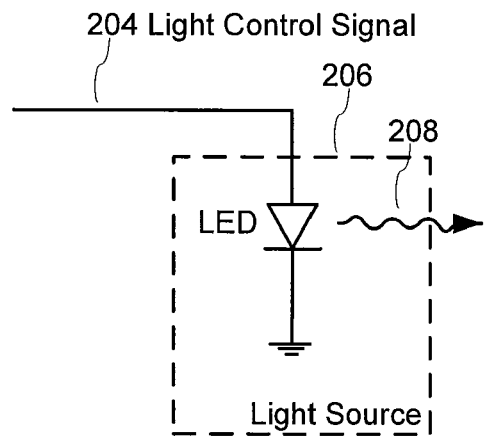
FIGS. 3A and 3B illustrate exemplary light sources for use in embodiments of the present invention.
Figure 3B:
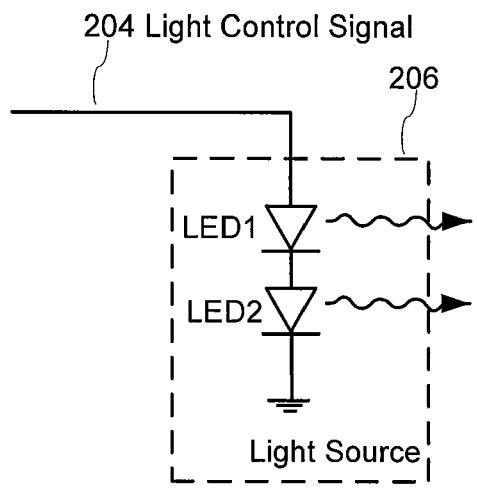

As mentioned above, a PPG sensor includes a light source and a light detector. FIGS. 3A and 3B illustrate exemplary light sources for use in the embodiments of the present invention. Referring first to FIG. 3A, exemplary light source 206 includes a single LED that produces light signal 208. The LED can be, for example, a model L53SRC/F red LED, or a model L53F3C infrared LED, both manufactured by Kingbright Corporation, City of Industry, Calif. Referring to FIG. 3B, a series of LEDs (e.g., LED1 and LED2) can be used to increase the amount of optical power in light signal 208. Separate LEDs can be used. Alternatively, dual emitter combination LEDs can be used, such as model DLED-660/905-LL5-2, manufactured by UDT Sensors, Inc., Hawthorne, Calif. In accordance with an embodiment, a pair of separately driven LEDs are used, where one of the LEDs is a red LED and the other is an infrared LED (which can be a near infrared LED), collectively allowing for pulse oximetry to be performed, providing for measures of blood oxygen saturation. The light source 206 can be driven by one or more light control signals 204, as shown in FIGS. 2A, 3A and 3B. In a conventional PPG sensor, the transmit light signal 208 would have a relatively constant average light intensity, though the light may be pulsed rapidly. Accordingly, in a conventional PPG sensor, the light control signal 204 is relatively constant when averaged over a period of the pulse train.

One of ordinary skill in the art will appreciate that the use of other LEDs and other light sources (e.g., a laser diode) are within the spirit and scope of the present invention. Further, it is possible that a green light (having a wavelength of about 530 nm) can be used instead of a red light.

Depending on the embodiment, the light source 206 may or may not include additional elements that are used, for example, to maintain a relatively constant current through an LED.

Figure 4:
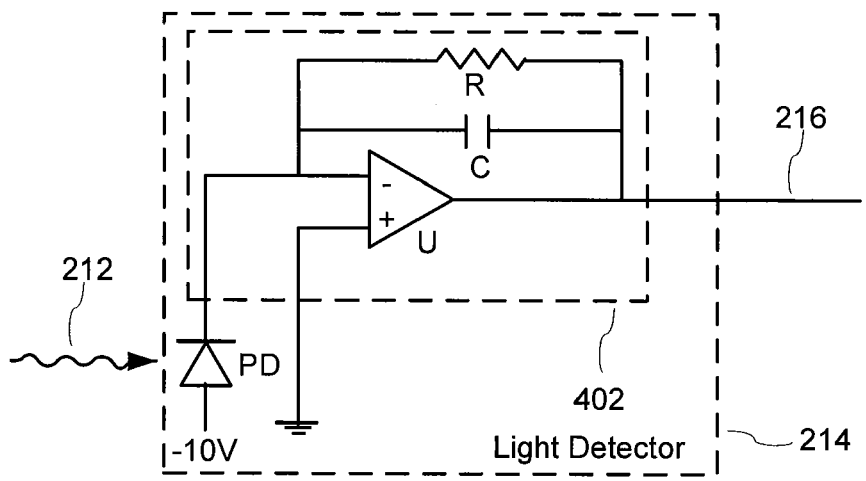
FIG. 4 illustrates an exemplary light detector for use in embodiments of the present invention.

FIG. 4 illustrates an exemplary light detector for use in embodiments of the present invention. Referring to FIG. 4, the exemplary light detector 214 includes a photodiode PD operated in a current sensing photoconductive mode feeding a transimpedance amplifier 402. Photodiode PD can be, for example, a model PIN-4.0-LLS, manufactured by UDT Sensors, Inc. The transimpedance amplifier 402 includes a resistor R, a capacitor C and an operational amplifier U, such as model ALD1701, manufactured by Advanced Linear Devices, Inc., Sunnyvale, Calif. The amplifier 402, including the RC circuit, performs low pass filtering and provides gain. It also serves as an antialiasing filter if ND conversion is applied directly to its output 216. One of ordinary skill in the art will appreciate that a photodiode PD can alternatively be operated in a voltage sensing configuration. Further, one of ordinary skill in the art will appreciate that the use of other photodiodes (e.g., an avalanche photodiode) and other light detectors (e.g., a photoresistor, a photodarlington, a phototransistor), are within the spirit and scope of the present invention. One of ordinary skill in the art will also appreciate that other amplifier configurations (e.g., an integrator amplifier or a transistor based amplifier) can be used in place of the transimpedance amplifier 402 shown in FIG. 4. An integrated photodiode/amplifier (e.g., a Burr-Brown OPT101, available from Burr-Brown Corporation, Tucson, Ariz.) can also be used.

Figure 1:
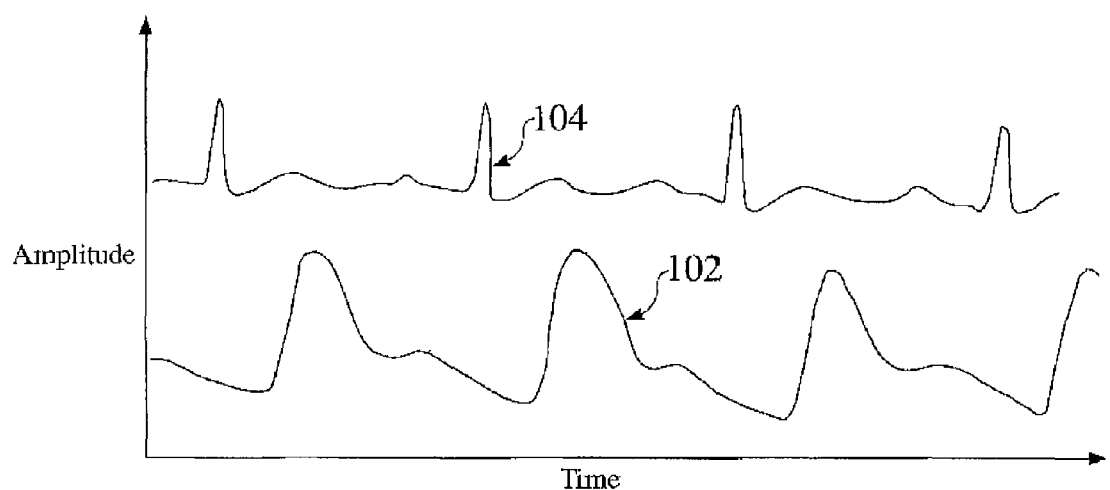
FIG. 1 illustrates exemplary PPG and ECG signals.
Figure 2B:
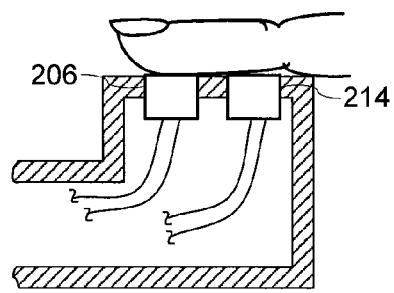
FIG. 2B is a simplified mechanical diagram illustrating a portion of an exemplary PPG sensor.

In a conventional PPG sensor (e.g., FIG. 2B), a constant average optical power is delivered by light source 206 (e.g., an LED) and plethysmography information (e.g., measurements of the waveform 102 shown in FIG. 1) is determined based on time varying optical power incident on light detector 214. A PPG sensor device can alternatively adjust the source of optical power such that a relatively constant average light intensity is detected at a light detector, as described in commonly assigned U.S. patent application Ser. No. 09/907,349 (Turcott), filed Jul. 16, 2001, entitled "Methods and Devices for Vascular Plethysmography Via Modulation of Source Intensity," which is incorporated herein by reference. The time-varying modulating signal (e.g., that controls the source power) can then be used as the plethysmography signal (i.e., the information signal), rather than the time-varying detected optical power. The time-varying detected optical power is used (e.g., in a feedback loop) to adjust the source intensity.

Figure 5:
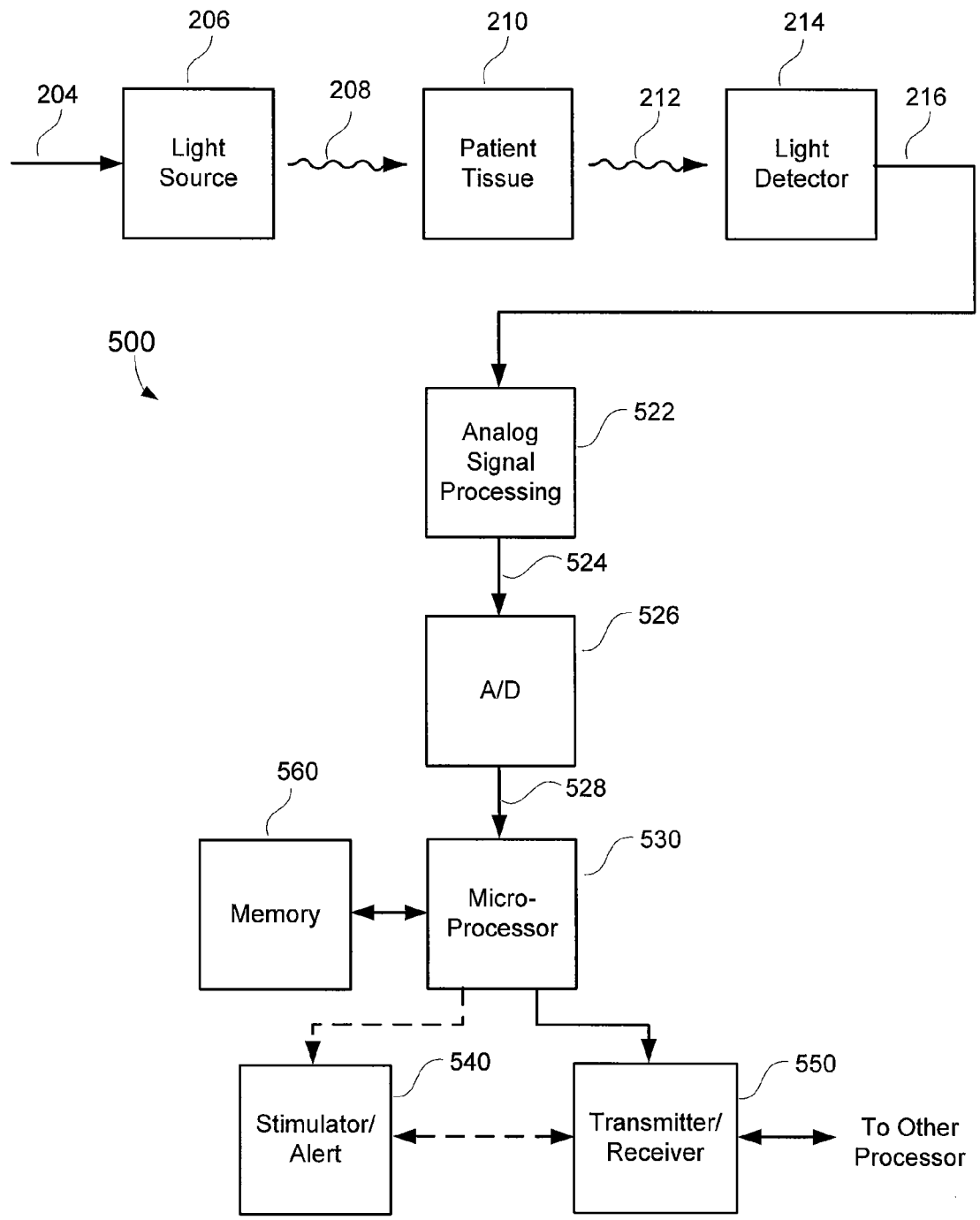
FIG. 5 illustrates an overview of a monitoring system according to an embodiment of the present invention.

FIG. 5 includes a block diagram that provides an overview of a monitor 500, according to an embodiment of the present invention. As will be explained in more detail below, the monitor 500 can be used to analyze hemodynamic signals, such as PPG signals. The light source 206 outputs a transmit light signal 208 of substantially constant average light intensity (as controlled by light control signal 204), though perhaps periodically or initially adjusted by an automatic gain control feature so that the light detector 214 is operating at a desirable point in its dynamic range. The light signal 208 is transmitted through and/or reflected by (depending on the embodiment) patient tissue 210. Receive light signal 212 is received by the light detector 214. The light intensity of the received light signal 212 is modulated by changes in blood volume in patient tissue 210. The light detector 214 produces a light detection signal 216 that is representative of the received light signal 212. The light output signal 216, which is likely an analog encoded information signal, is preferably filtered and amplified by an analog signal processor block 522. A filtered and amplified signal 524 is then provided to an analog to digital converted (A/D) 526, which provides a digital encoded plethysmography information signal 528 to a microprocessor 530.

The microprocessor 530 analyzes the plethysmography signals as represented by the encoded information signals 528. According to embodiments of the present invention, the microprocessor 530 performs the averaging used in embodiments of the present invention. The microprocessor 530 may also perform respiratory monitoring, pacing interval optimization, etc., in accordance with embodiments of the present invention.

If the monitor 500 is not implanted, the light source 206 and the light detector 214 can be made small and can conveniently attach to a peripheral portion of the body, such as a finger, toe, or ear. Thus, patients are likely to tolerate regular use of these sensors for an extended period of time, such as during sleep each night. Particular embodiments include a finger cuff, a wristband, a configuration resembling a watch, and a configuration resembling a clip-on earring. The light source 206 and light detector 214 could be tethered to a larger unit containing the bulk of the electronic circuitry (e.g., the microprocessor 530 and a memory 560). In this case, the monitor 500 would be worn primarily when the patient is sleeping. Alternatively, data (e.g., from the light detector 214, ND 522, or microprocessor 530) could be continuously or periodically be telemetered to a processor (e.g., the microprocessor 530 or some other processor), which might be worn on the patient's clothing or located in the patient's home and/or office. In this case, the monitor could be worn both during sleep and during activity. Nevertheless, despite the cost advantages of an external embodiment, such an approach necessarily requires patient cooperation. Because of the disadvantages associated with this it may be preferable that the monitor 500 is an implanted extravascular configuration. In addition, the monitoring function just described can be integrated with a pacemaker or ICD in order to enhance the therapy delivered by these devices. However, it should be clear that many embodiments of the present invention are not limited to implantable implementations.

The monitor 500 can also include a transmitter/receiver 550 (i.e., a telemetric circuit) and a memory 560. If the monitor 500 is chronically implanted, transmitter/receiver 550 enables the operating parameters of the monitoring device 500 to be non-invasively programmed into the memory 560 through telemetric communications with an external device, such as a programmer or transtelephonic transceiver. The transmitter/receiver 550, which is preferably controlled by the microcontroller 530 (which is likely a processor), also enables the monitor 500 to communicate with other types of external processors. For example, the transmitter/receiver 550 enables plethysmography information and status information relating to the operation of the device 500 (e.g., as contained in the microcontroller 530 and/or memory 560) to be sent to an external device (e.g., a remote processor or diagnostic system analyzer) through an established communication link. The microprocessor 530 can analyze a hemodynamic signal, and the transmitter/receiver 550 can transmit the information to another processor as appropriate. The transmitter/receiver 550 can additionally, or alternatively, transmit waveform information to an external device (e.g., a remote processor) that can analyze a hemodynamic signal based on the information. Alternatively, the encoded information signals (e.g., the light detection signal 216) can be transmitted directly to an external device (e.g., a remote processor), and the external device can perform appropriate analysis.

For examples of a transmitter/receiver 550 (also known as a telemetric circuit) of a chronically implantable device, see U.S. Pat. No. 4,809,697, entitled "Interactive Programming and Diagnostic System for use with Implantable Pacemaker" (Causey, III et al.), and U.S. Pat. No. 4,944,299, entitled "High Speed Digital Telemetry System for Implantable Device" (Silvian), each of which is hereby incorporated herein by reference. Another example of a telemetric circuit for use in a chronically implantable device is the TR1000 transceiver manufactured by RF Monolithics, Dallas, Tex. The TR 1000 is a single-chip, low-power, 916.5 MHz transceiver. The operating frequency of 916.5 MHz is desirable because of the modest requirements on antenna size it imposes.

The monitor 500 can also include a stimulation/alert block 540, that informs a patient, physician, clinician and/or any other person (or processor) of the status of the patient. If the monitor 500 is implanted, an alert block 540 is preferably an external device that telemetrically communicates with the microprocessor 530 (e.g., using transmitter/receiver 550). The stimulation/alert block 540 can include an indicator that provides, for example, an acoustic, mechanical vibration, optical and/or electrical indication and/or stimulation. Such an alert indicator can be triggered when a criterion (e.g., threshold) is satisfied (e.g., exceeded), as discussed below. In one embodiment stimulation/alert 540 includes an inductive coil that generates both sound and mechanical vibration. In an alternative embodiment, the function of the stimulation/alert 540 is incorporated into the microprocessor 530 and the transmitter/receiver 550.

Figure 6:
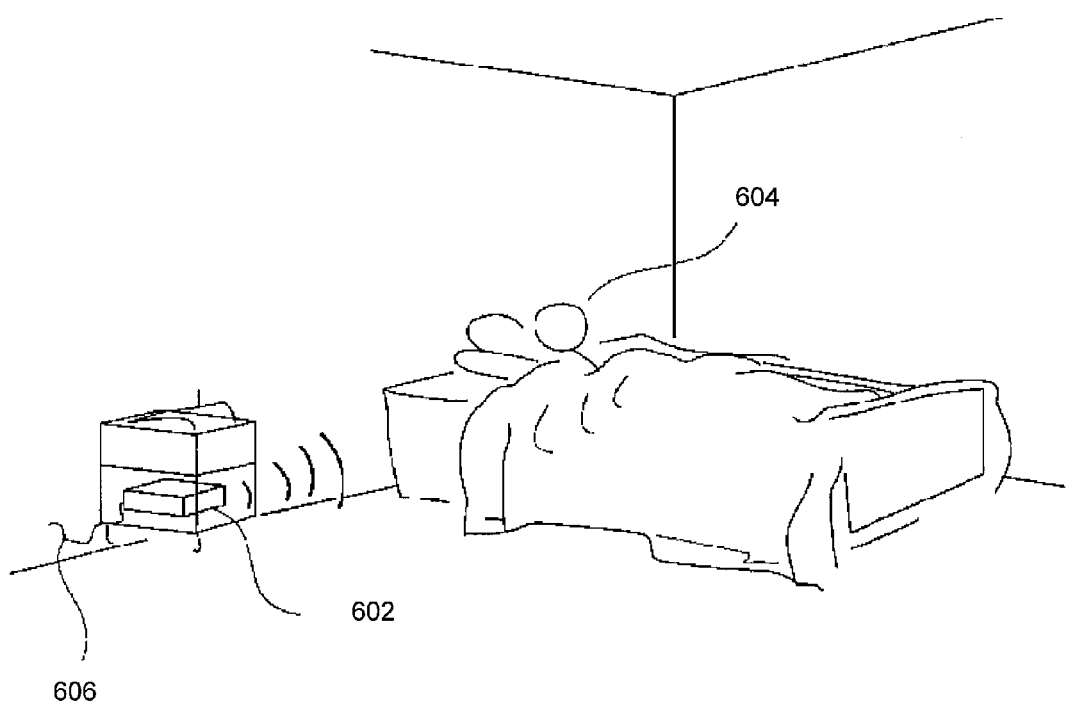
FIG. 6 illustrates placement of an external telemetry unit in, for example, a patient's bedroom.

FIG. 6 illustrates placement of an external telemetry (i.e., transmitter/receiver) unit 602 in, for example, a patient's bedroom or a physician's or clinician's office. The external telemetry unit 602, using telemetry at a distance, allows the transfer of data to and from the monitor 500 if it is a chronically implanted device or a device that clips on the finger, toe or earlobe, without the active participation of the patient 604 or a clinician. The external telemetry unit 602 is preferably positioned in a location(s) regularly frequented by the patient, such as the patient's bedroom, office, and/or automobile. The external telemetry unit 602 can be in communication (e.g., through a telephone line 606, network connection and/or wireless links) with a central location for further processing or review (e.g., by a clinician). Alternatively, the external telemetry unit can be in a physician's or clinician's office so that data can be downloaded from an implantable monitor 500 whenever the patient visits the office. The data that is downloaded may have already been analyzed by the implantable monitor, or the data that is downloaded can be raw data that is analyzed after it is downloaded from the implantable monitor.

A PPG sensor can use a single wavelength of light, or a broad spectrum of many wavelengths. In the alternate embodiments, the light source can be any source of radiant energy, including laserdiode, heated filament, and ultrasound transducer. The detector can be any detector of radiant energy, including phototransistor, photodetector, ultrasound transducer, piezoelectric material, and thermoelectric material.

Reducing Data Acquisition, Processing and/or Power Consumption

Embodiments of the present invention relate to reducing the amount of data required (e.g., produced and/or stored) to analyze a hemodynamic signal, such as a photoplethysmography (PPG) signal or an arterial pressure signal. Embodiments of the present invention also relate to reducing the amount of power consumption and processing that is required to produce and/or analyze such data. Embodiments of the present invention are further directed to reducing the amount of data that may be stored for later analysis of the data.

Figure 7:
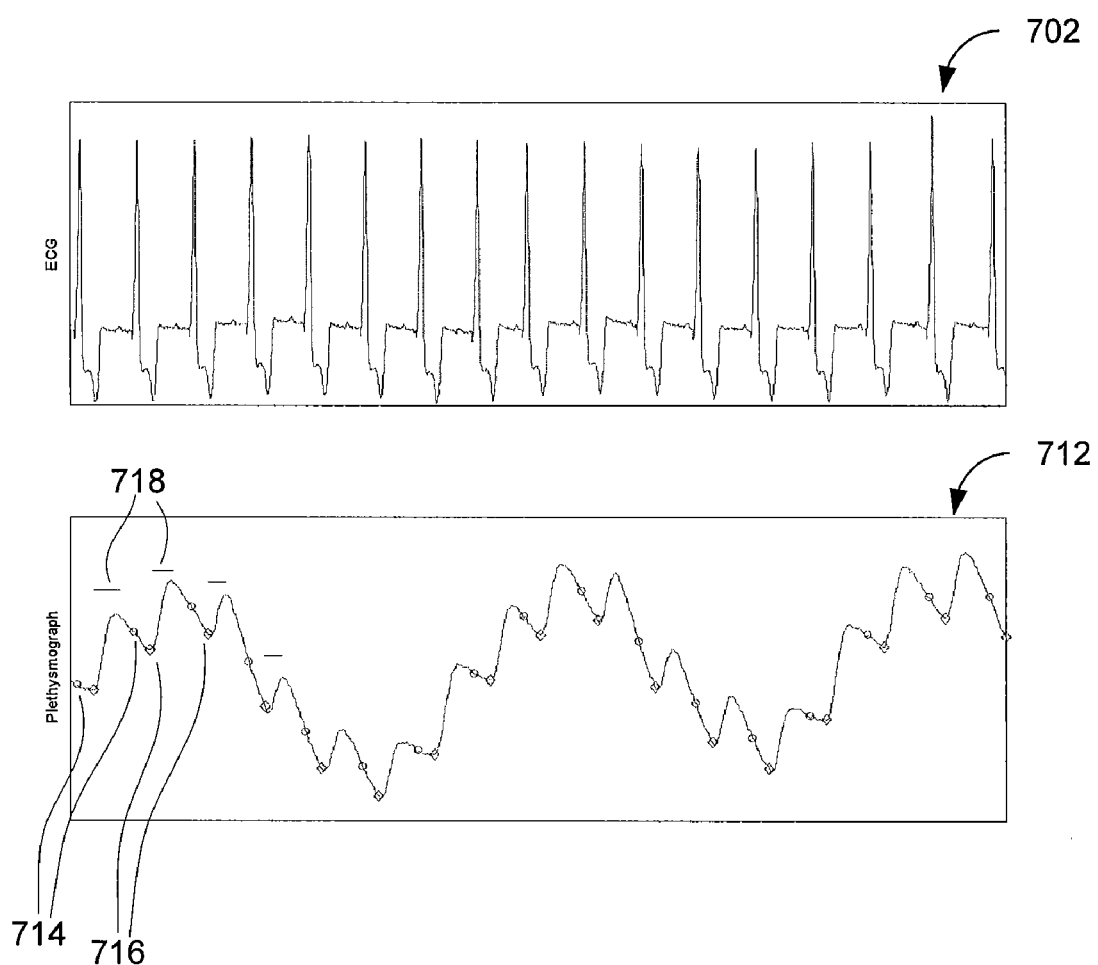
FIG. 7 illustrates simultaneously recorded ECG and PPG waveforms, which are useful for describing embodiments of the present invention.

FIG. 7 illustrates simultaneously recorded ECG, and PPG signals, labeled 702 and 712, respectively. In this plot, a positive deflection of the PPG signal 712 is caused by increased light absorption by the tissue, and a corresponding decrease in detected light, as when a cardiac pulse causes an expansion of peripheral vascular volume. Conversely, a negative deflection of the PPG waveform results from a decrease in tissue light absorption, and a corresponding increase in detected light, as when vascular volume is reduced. Slow oscillation in the baseline of the PPG signal 712 is due to positive-pressure ventilation, and likely results from both the modulation of peripheral venous volume induced by the changing intrathoracic pressure, and the modulation of the arterial volume secondary to ventilation-induced changes in arterial pressure, apparent in the waveform 712. Of lower amplitude in this example, but still clearly apparent, are the pulsations in the PPG waveform 712 due to the arrival of the cardiac pulse at the periphery. Thus, effects arising from the modulation of both arterial and venous vascular volumes can be seen in the raw PPG signal 712.

Figure 2C:
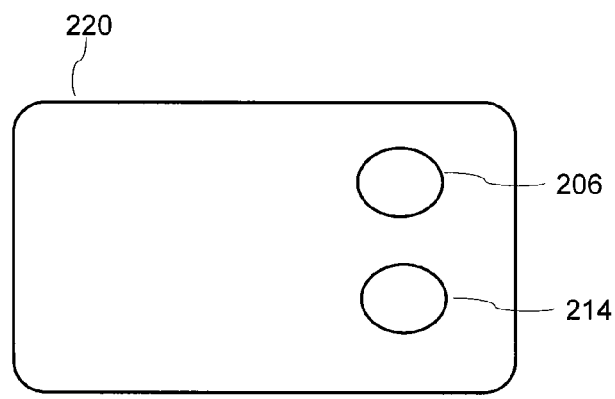
FIG. 2C is a simplified mechanical diagram illustrating an exemplary implantable PPG sensor.

Referring back to FIGS. 2, 4 and 5, the PPG signal 712 is an example of the varying analog voltage light detection signal 216 that is produced by the light detector 214. As mentioned above, such a PPG signal is typically filtered, amplified and converted to a digital signal using an analog-to-digital (A/D) converter (not necessarily in the order). For example, the signal may be sampled at 500 Hz (i.e., 500 samples per second) using a high resolution A/D converter, and then the samples may undergo relatively intensive post-acquisition digital filtering (e.g., using a 1000-point filter). This relatively high sampling rate and relatively intensive filtering consumes battery power and processing resources. While this may not be much of a concern with non-implanted PPG devices (e.g., such as the one shown in FIG. 2B), minimizing power consumption and processing is very important when it comes to implantable devices. This is in part because invasive surgery is required to replace the battery of an implanted device. Accordingly, there is a desire to reduce, and hopefully minimize, both the number of samples that are acquired, and the associated processing of such samples, which in turn will reduce and hopefully minimize power consumption.

Producing One Sample Per Cycle of a Cyclical Body Function

In accordance with embodiments of the present invention, rather than continuously sampling at a high rate, the PPG signal (e.g., signal 712) is sampled once for each heart beat. For example, in accordance with an embodiment of the present invention, the sampling of a PPG signal can be triggered by a sensed or paced event. More specifically, the sensed event can be a ventricular or atrial event, such as a contraction. Similarly, the paced event can be a ventricular pace or an atrial pace. In some embodiments, the PPG signal is sampled at a fixed delay after the sensed or paced event.

For example, assume a patient's heart beat is 60 beats per minute (i.e., 1 beat per second), and that sampling of the PPG signal is 500 Hz (i.e., 500 samples per second). This would result in 500 samples per heart beat. In contrast, with the just described embodiment of the present invention, only one sample is obtained per heart beat. Thus, the amount of acquired data is reduce by a factor of 500.

Referring to FIG. 7, the open circles 714 represent samples that were triggered by a ventricular contraction. In some embodiments, the PPG signal 712 can be sampled at a fixed delay after the ventricular event, as illustrated by the diamonds 716 in FIG. 7.

The effects of cardiac pulsations are reduced by sampling the signal at the same instant or point in each cardiac cycle (which is preferably during diastole). Because the effects of cardiac pulsations are sufficiently reduced, the need for filtering of the sample is avoided (although filtering can still be performed if desired). Further, the number of A/D conversions is significantly reduced (e.g., by a factor of 500 in this example). In addition, if sample data is being stored for later analysis, the amount of stored data is significantly reduced.

A systolic pulse does not reach a PPG sensor at a periphery for approximately 200 milliseconds, resulting in a PPG signal being essentially constant at the time of ventricular contraction. By sampling the PPG signal during diastole, when the slope of the PPG signal is small (rather than during the steep up slope during systole), the effects of cardiac pulsations can be further reduced.

The above described embodiments can be applied to hemodynamic signals other than PPG signals. For example, embodiments of the present invention can also be used reduce the amount of data processing and power required to analyze a pressure signal. Such a pressure signal can be produced in various manners. For example, a pressure catheter can be placed within an artery to obtain an arterial pressure signal. Alternatively, a hollow lumen catheter that is placed within an artery can be in communication with an extravascular pressure transducer, thereby producing an arterial pressure signal. In yet another alternative, a pressure transducer can be placed on a pacing or defibrillation lead that is positioned in the right ventricle, allowing an RV pressure signal to be recorded. Such a pressure transducer can similarly be placed in the right atrium, which would enable the acquisition of a right atrial pressure signal. In still another alternative, thoracic impedance or impedance of peripheral tissue can be used to assess pulmonary or peripheral edema, respectively. In a further alternative, thoracic impedance can be used to estimate cardiac output and stroke volume, as is done in a commercially available deviced produced by CardioDynamics, San Diego, Calif. These are just a few examples, which are not meant to be limiting.

Figure 8A:
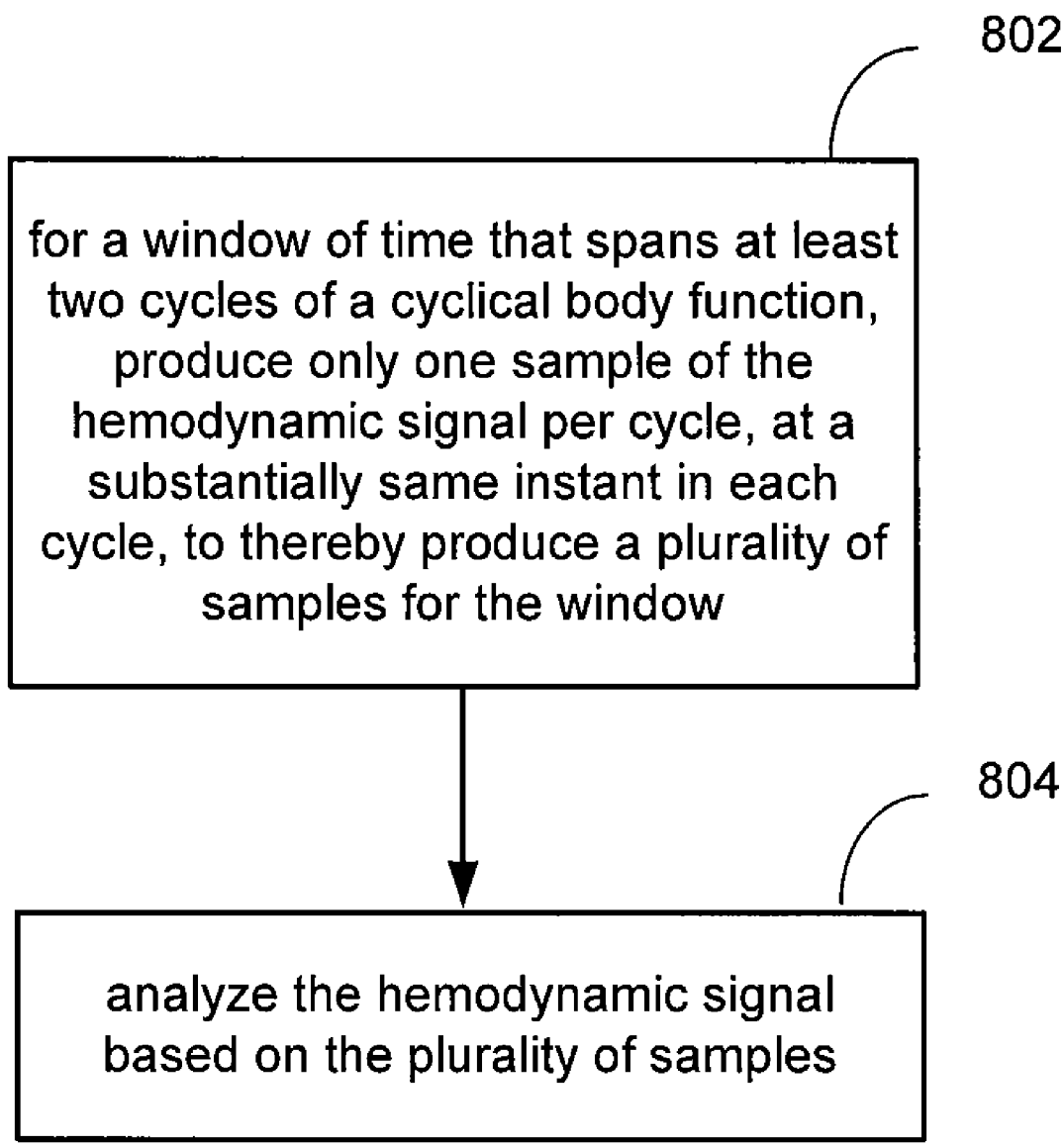
FIGS. 8A and 8B are high level flow diagrams useful for describing embodiments of the present invention where only one sample of a hemodynamic signal is produced per cycle of a cyclical body function.

The above described embodiments of the present invention will now be summarized and explained in further detail with reference to the high level flow diagram of FIG. 8A. Referring to FIG. 8A, at a step 802, for a window of time that spans at least two cycles of a cyclical body function, one sample of the hemodynamic signal is produced per cycle. In order to reduce (and hopefully eliminate) the noise due to the cyclical body function, the samples are produced at a substantially same instant in each cycle. To further ensure that the effects of cardiac pulsations are minimized, the samples can be produced during diastole, where the slope of the hemodynamic signal is small, as has been explained above.

Step 802 results in a plurality of samples for the window. Next, at a step 804, the hemodynamic signal is analyzed based on these plurality of samples. As mentioned above, the hemodynamic signal can be, e.g., a PPG signal or an arterial pressure signal. Additional details of step 804 are discussed below.

In accordance with embodiments of the present invention, the cyclical body function referred to in step 802 is heart beat, and the cycle referred to is a cardiac cycle. In other words, step 802 can be performed by producing one sample a hemodynamic signal per cardiac cycle, at substantially the same instant in each cardiac cycle, for a window of time that spans at least two cardiac cycles.

In order to trigger the sampling at substantially the same instant in each cardiac cycle, the sampling can be triggered in response to a specific cardiac event, which can be detected based on an ECG signal that is being simultaneously produced and monitored. For example, in accordance with embodiments of the present invention, the sampling is in response to sensing a ventricular contraction. This can include sampling at the instant the ventricular contraction is sensed, or a fixed delay after sensing the ventricular contraction. In accordance with other embodiments, the sampling is in response to a paced event, such as ventricular pace, assuming the patient's heart is being paced. This can include sampling at the instant of the ventricular pace, or a fixed delay after the ventricular pace. Alternatively, sampling can be in response to an atrial event, such as an atrial contraction or an atrial pace. In a similar manner as described above, this may include sampling when the atrial event is sensed/paced, or a fixed delay thereafter.

Additional details of step 804 will now be described, assuming the cyclical body function referred to in step 802 is heart beat, and the cycle referred to is a cardiac cycle. In accordance with embodiments of the present invention, step 804 includes monitoring respiration based on the plurality of samples produced at step 802. For example, this can include determining a rate of respiration based on the plurality of samples.

One way to accomplish this is to determine an average of the plurality of samples, so that the average can serve as a threshold. Then, the plurality of samples can be compared to the average to thereby determine a number of threshold crossings. The rate of respiration can then be determined based on the number of threshold crossings, e.g., by counting the number of crossings from above the threshold to below the threshold (or vice versa) for the window of time, and converting that number to a conventional scale, such as breaths per minute.

Another way to accomplish this is to determine an average of the plurality of samples. Then, the plurality of samples can be normalized by subtracting the average from each of the plurality of samples, to thereby produce a plurality of normalized samples. The plurality of normalized samples can then be compared to zero to thereby determine a number of zero crossings. Then, in a similar manner to that just described, the rate of respiration can be determined based on the number of zero crossings.

In accordance with other embodiments of the present invention, respiratory effort can be determined based on the plurality of samples. This can be accomplished, e.g., by determining a peak-to-peak amplitude based on the plurality of samples. The peak-to-peak amplitude is indicative of the respiratory effort in that an increase in peak-to-peak amplitude is indicate of an increased respiratory effort, and a decrease in peak-to-peak amplitude is indicative of a decrease in respiratory effort.

Returning to the discussion of step 802, in alternative embodiments the cyclical body function referred to in step 802 can be respiration, and each cycle can be a respiratory cycle. In such embodiments the sampling of the hemodynamic signal can be triggered in response to sensing a respiratory event, such as the end or beginning of inspiration or respiration. As with the previous discussed embodiments, sampling can be triggered at the instant of detecting a specific respiratory event, or a fixed delay after the specific respiratory event. Such specific events may detected, e.g., using measures of thoracic impedance which are often determined by an implanted monitor and/or stimulation device. In sampling once per respiratory cycle the variability in the PPG, pressure, or other hemodynamic signal that is induced by respiration or ventilation is avoided, and the need for filtering is reduced as is the processing and volume of acquired data. Eliminating respiratory variability is important, for example, in obtaining relative estimates of average vascular volume from a PPG signal, obtaining estimates of average pressure from a pressure signal, or obtaining estimates of thoracic impedance (in order to monitor for pulmonary edema) from a impedance measuring system. These examples illustrate some of the applications of synchronously sampling with a cyclical physiologic process, and are not meant to be limiting.

As mentioned above, the hemodynamic signal that is being sampled can be, e.g., a PPG signal, a pressure signal, or a signal representative of pulmonary or peripheral edema, such as impedance. Where the hemodynamic signal is a PPG signal, the PPG signal can be produced using a light source and light detector that are not implanted in a patient. However, embodiments of the present invention are more likely to be implemented when the PPG signal is produced using an implanted light source and light detector, which are likely implemented as part of an implanted monitor and/or stimulation device. This is because reducing amounts power, processing and data storage is more important for implanted devices.

A generally continuous PPG signal can be produced by a PPG sensor, e.g., by continually driving the light source of the PPG sensor, or pulsing the light source multiple times per cycle of the cyclical body function. In accordance with embodiments of the present invention just described above, the corresponding output of the light detector of the PPG sensor is only sampled once per cycle of the cyclical body function (e.g., once per cardiac cycle, or once per respiratory cycle). Thus, the extent of sampling and the number of samples produced (and possibly stored) is reduced. Also, because the sampling is at substantially the point in each cycle, there is no need to low pass filter the samples (for reasons explained in detail above), further reducing processing and power consumption.

Continually driving or pulsing the light source (i.e., driving the light source with voltage or current pulses) can consume a significant amount of power. Accordingly, it may be preferable to minimize the pulsing of the light source, and thus, not produce a generally continuous PPG signal output. Rather, the light source of the PPG sensor can be pulsed only once per cycle of the cyclical body function (at substantially the same instant in each cycle), causing the light detector to produce only one output per cycle (at substantially the same instant in each cycle). This is sufficient for the above discussed embodiments, since only one sample per cycle need be produced, as has been described in detail above. This will further reduce power consumption, because the light source of the PPG sensor will consume less power if it is driven less frequently. It is noted that step 802 is meant to encompass this approach.

As mentioned above, rather than being a PPG signal, the hemodynamic signal that is being analyzed can be an arterial pressure signal. Such an arterial pressure signal can produced using a pressure transducer placed within an artery. Alternatively, the arterial pressure signal is produce using a hollow lumen catheter that is placed within an artery and an extravascular pressure transducer in communication with the catheter. In yet another alternative, a pressure transducer is placed on a pacing or defibrillation lead that is positioned in the right ventricle, allowing an RV pressure signal to be recorded. In still another alternative, thoracic impedance or impedance of peripheral tissue can be used to assess pulmonary or peripheral edema, respectively.

Depending on implementation, the time window referred to in step 802 can span, e.g., a predetermined time interval, a predetermined number of cardiac cycles, or a predetermined number of respiratory cycles, any of which should be at least as long as two cycles of the relevant cyclical body function.

At least two samples are produced at step 802, by producing a sample only once per cycle. While such samples can be obtained during consecutive cycles of the cyclical body function (e.g., during consecutive cardiac cycles), this is not required. That is, during the sampling of the hemodynamic signal only once per cycle at step 802, the cycles that are sampled need not be consecutive cycles. For example, a sample could be produced every other cycle, or even less uniformly and less frequently than that. In estimating pulmonary edema, for example, one may elect to sample once a night. While this may not be preferred, it is noted that step 802 is intended to cover such approaches.

It is noted that step 802 can be repeated a number of times (i.e., for a number of windows of time) before the samples produced at step 802 are analyzed at step 804. For example, sampling at step 802 can be performed by an implanted device over a relatively long period of time, and then the data (e.g., samples) can be analyzed at a later time at step 804. The analysis at step 804 can be performed by the implanted device, or the data obtained at step 802 can be downloaded (e.g., through telemetry) to an external device that performs step 804. In this manner, with growing interest in disease monitoring based on data obtained from implantable devices (as well as external devices), embodiments of the present invention can help alleviate problems associated with acquiring large amounts of hemodynamic data over relatively long periods of time between downloads to an external device.

Figure 8B:
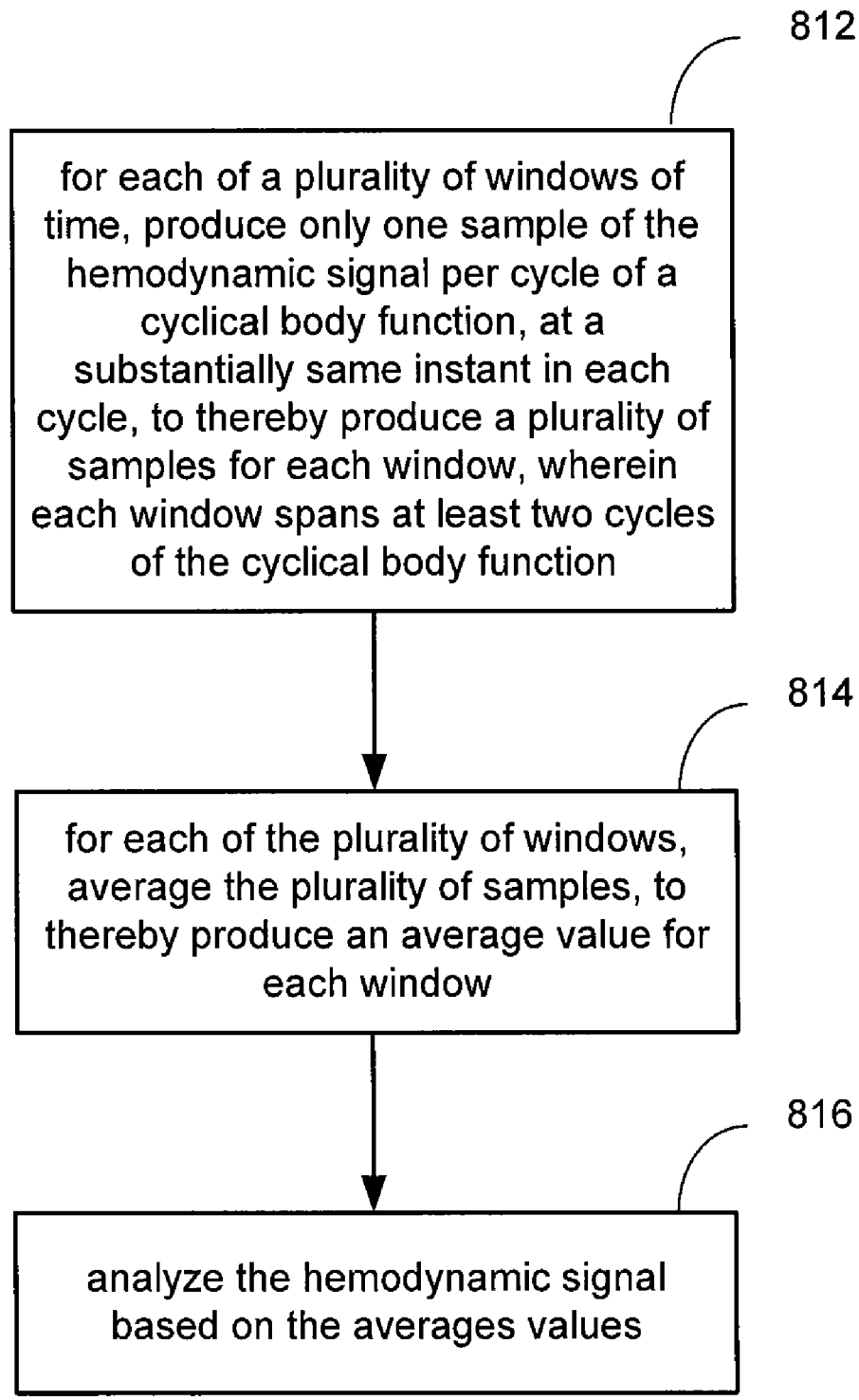

The high level flow diagram of FIG. 8B will now be used to provide additional details about embodiments where data is collected for multiple windows of time.

Referring to FIG. 8B, at a step 812, for each of a plurality of windows of time that each spans at least two cycles of the cyclical body function, only one sample of a hemodynamic signal is produced per cycle of a cyclical body function, at a substantially same instant in each cycle. In this manner, a plurality of samples is produced for each window. As was discussed above with reference to step 802, during the sampling of the hemodynamic signal only once per cycle at step 812, the cycles that are sampled within each window need not be consecutive cycles. As with the discussion of FIG. 8A the cycles could be, for example, cardiac cycles or respiratory cycles. Similarly, the hemodynamic signal can be, for example, a PPG signal, an arterial or right ventricular pressure signal, or an impedance signal reflective of pulmonary or peripheral edema. In a similar manner to that discussed above with reference to step 802, the sampling can be in response to a specific cardiac event or a specific respiratory event. This may include sampling a fixed delay after the specific event.

The hemodynamic signal can then be analyzed based on the samples produced at step 812. More specifically, at a step 814, for each of the plurality of windows, the plurality of samples can be averaged to thereby produce an average value for each window. At a step 816, the hemodynamic signal can then be analyzed based on the averages values. Other operations that characterize the amplitude of the data can be used. For example, the data can be summed without dividing by the number of data points that were included in the sum. If this number is fixed then different sums can be compared directly, and treated as if they were true averages. Another alternative is to use the median of the plurality of samples rather than the mathematical average. For simplicity we refer to an average but this is not meant to imply that only a precise mathematical average is acceptable. Rather, by 'average' we mean any characterization of the plurality of samples that represents the ensemble properties.

In accordance with specific embodiments of the present invention, the hemodynamic signal of which samples are produced in step 812 is a PPG signal, and step 816 includes monitoring changes in mean arterial pressure (MAP) based on changes in the average values determined at step 814. Commonly invented and assigned U.S. patent application Ser. No. 10/802,009, entitled "Methods, Systems and Devices for Monitoring Mean Arterial Pressure" filed Mar. 15, 2004, which is incorporated herein by reference, explains how and why a PPG signal can be used to monitor changes in mean arterial pressure. In the just mentioned '009 application, each of a plurality of segments of a PPG signal is averaged, to thereby produce a corresponding plurality of average values, and changes in mean arterial pressure are monitored based on changes in the average values. Embodiments of the present invention can be used to improve upon such embodiments by reducing the amount of data and processing used to monitor mean arterial pressure.

In accordance with embodiments of the present invention, monitoring the changes in mean arterial pressure includes recognizing a change in the average values that corresponds to an increase in arterial volume as an increase in mean arterial pressure. Alternatively, or additionally, monitoring changes in mean arterial pressure includes recognizing a change in the average values that corresponds to a decrease in arterial volume as a decrease in mean arterial pressure.

Further, pacing interval optimization can be based on the monitored mean arterial pressure. For example, when comparing two different AV delays, it can be concluded that the AV delay producing the greatest increase in mean arterial pressure is the better AV delay, meaning that it allows the heart to function with greater mechanical efficiency. In one embodiment baseline pacing is provided with a specific AV delay, and periodically the AV delay is changed to test values with the pacing delivered at the test value for a brief amount of time. The change in average arterial volume is assessed by photoplethysmography as the changes in AV delay are made. The AV delay that yields the greatest increase in blood volume is then selected as the optimal AV delay. This is just one example of how embodiments of the present invention can be used for pacing optimization.

In accordance with other specific embodiments of the present invention, the monitored changes in mean arterial pressure can be used to select a type of anti-arrhythmia therapy, when an arrhythmia is detected. Arrhythmias are irregular heartbeats that feature either very rapid ventricular contractions (tachycardia), an excessively slow heartbeat (bradychardia) or, commonly, extra or "premature" beats.

The most lethal arrhythmia is ventricular fibrillation (VF), in which the ventricles undergo persistent and disorganized activation. In this arrhythmia the heart is not capable of pumping blood. Mean arterial blood pressure quickly falls, and perfusion of the vital organs ceases. Once VF begins, death will soon follow unless the arrhythmia is successfully terminated. ICDs are generally quite effective at detecting VF because of its exceedingly rapid electrical rate. Once VF is detected, the ICDs are appropriately designed to deliver a high-voltage shock, which is the most aggressive therapy. Some arrhythmias do not necessarily require electrical therapy, e.g., atrial fibrillation (AF) when it is hemodynamically stable, that is, when it doesn't compromise mean arterial pressure. Other arrhythmias require electrical therapy, but it need not be aggressive. For example, a low-rate ventricular tachycardia (VT) is often hemodynamically stable. For these arrhythmias, low-voltage anti-tachycardia pacing or low-energy cardioversion may terminate the arrhythmia but consume less battery power and cause less discomfort to the patient than the high-voltage shocks used to terminate VF. Convention ICDs are typically programmed to deliver aggressive therapy as quickly as possible for VF, to attempt to terminate VT with less aggressive therapy, and to withhold electrical therapy for AF. The problem is that for many rhythms, the conventional ICD has no way of knowing whether the hemodynamic status of the patient has been compromised because the same electrical rhythm can have different hemodynamic consequences in different patients, or in the same patient at different points in time.

Thus, using embodiments of the present invention to detect significant decreases in mean arterial pressure would allow an ICD to select aggressive, high-voltage therapy only when necessary. Similarly, recognizing that mean arterial pressure has not been significantly compromised despite the detected onset of an arrhythmia would allow the device to attempt less aggressive techniques of arrhythmia termination. More specifically, at step 816, changes in average values can be compared to a threshold, and a type of anti-arrhythmia therapy can be selected based on whether the changes in the average values exceed the threshold. This may include, for example, selecting a high voltage therapy if a change in the average values exceeds the threshold, and selecting a lower voltage therapy (or no electrical therapy) if a change in the average values does not exceed the threshold.

Embodiments of the present invention can be used for pacing interval optimization, as will now be discussed in further detail. In accordance with embodiments of the present invention, the hemodynamic signal referred to in step 812 is produced as a heart is paced using a plurality of different sets of pacing intervals, with each of the windows corresponds to a different one of the sets of pacing intervals. Each set of pacing interval parameters can include one or more pacing intervals (i.e., delays). The initiating event, from which the interval/delay is specified, can be either a delivered pace pulse, or a sensed depolarization. The pacing interval parameters can be used, e.g., for multi-site pacing, and may include, e.g., an atrio-ventricular (AV) delay, an interventricular delay and/or an interatrial delay. Pacing intervals can define an intra-chamber pacing delay or an inter-chamber pacing delay. Pacing intervals can be used for two, three or four chamber pacing. These are just a few examples, which are not meant to limit the scope of the present invention.

By having each of the windows corresponds to a different one of the sets of pacing intervals, a different average value (one for each window) is produced for each set of pacing intervals, at step 814. Accordingly, step 816 can include performing pacing interval optimization based on the average values, or more specifically, based on changes in the average values. For example, step 816 can include selecting one of the plurality of sets of pacing intervals, as a preferred set, based on the average values. This may include, e.g., selecting the set of pacing intervals that produced the greatest average as the preferred set.

One of ordinary skill in the art will appreciate that at steps 804 and 816 a hemodynamic signal could be analyzed in manners other than those described in detail above, while still being within the spirit and scope of the present invention.

Using Analog Circuitry to Detect Peak-to-Peak Amplitude

Embodiments of the present invention are also directed to reducing the amount of sampling and processing required to detect the peak-to-peak amplitude of a hemodynamic signal, such as a PPG signal or an arterial pressure signal. Conventionally, such signals would be continuously sampled to produce numerous samples from which minimum and maximum amplitudes could be identified, and peak-to-peak amplitude could then calculated based on the maximum and minimum. Embodiments of the present invention, which will now be described with reference to the high level flow diagram of FIG. 9, use analog circuitry to reduce the amount of sampling, processing and power consumption required to detect peak-to-peak amplitudes.

Figure 9:
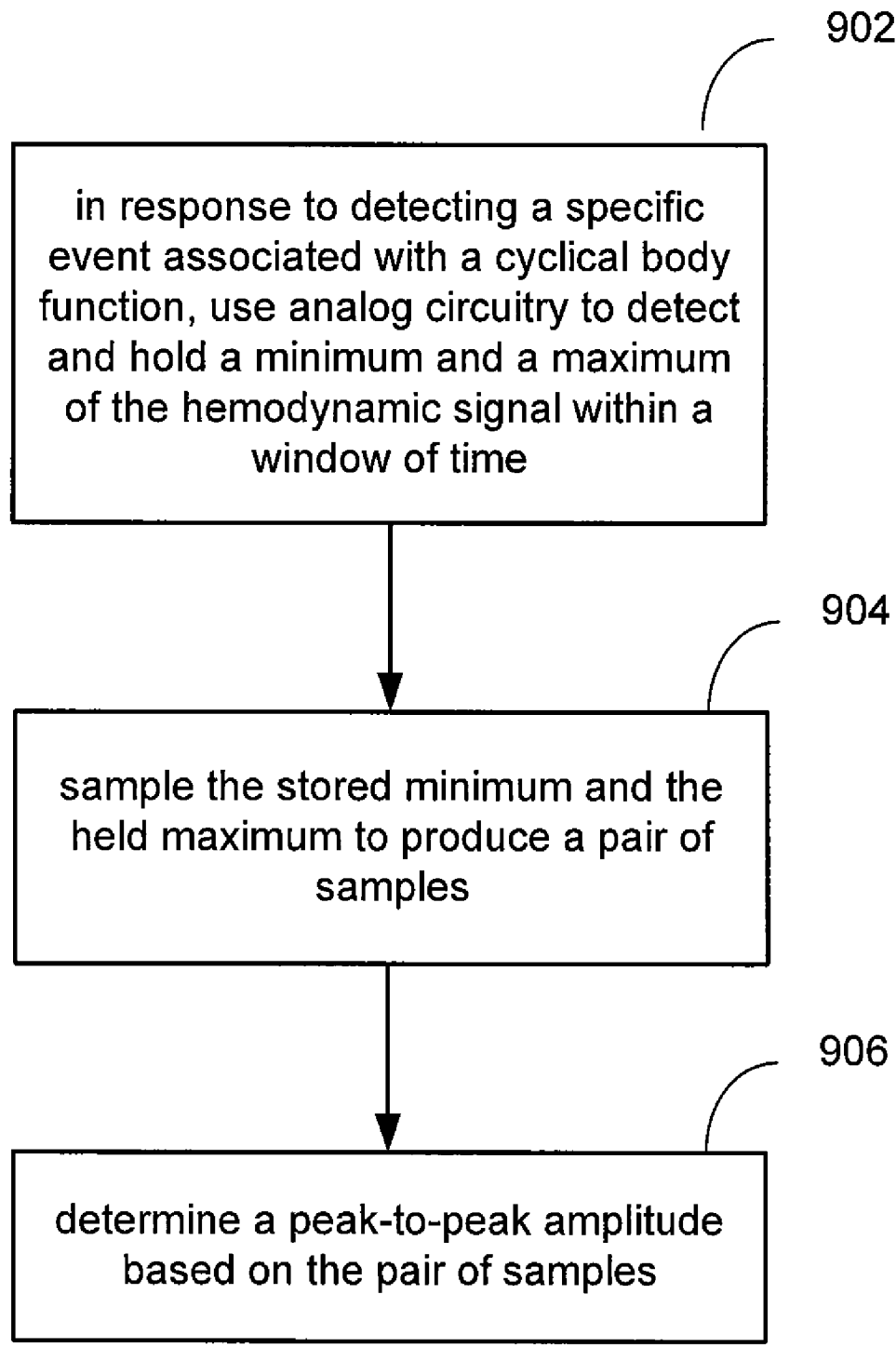
FIG. 9 is a high level flow diagram useful for describing embodiments of the present invention where analog circuitry is used to efficiently determine peak-to-peak amplitude of a hemodynamic signal.

Referring to FIG. 9, at a step 902, in response to detecting a specific event associated with a cyclical body function, analog circuitry is used to detect and hold a minimum and a maximum of the hemodynamic signal within a window of time. The analog circuitry can include a first analog peak detector to detect and hold the maximum, and a second analog peak detector to detect and hold the minimum. Analog peak detectors are well known and thus need not be described in further detail.

At a step 904, only the held minimum and the held maximum are sampled by an ND converter to produce a pair of digital samples.

Then, at a step 906, a peak-to-peak amplitude is determined based on the pair of samples.

As with previous embodiments discussed above, the cyclical body function can be heart beat, and the specific event that initiates the using of the analog circuitry can be, for example, sensing a ventricular or atrial contraction, or a ventricular or atrial pace. The cyclical body function can alternatively be respiration, and the specific event that initiates the using of the along circuitry can be expiration or inspiration. Similar to previous embodiments, the use of the analog circuitry can be triggered a fixed delay after a specific event.

Continuously Sampling During Short Windows

In accordance with the following embodiments of the present invention, rather than simply producing only one sample per cycle of a cyclical body function, the number of samples per cycle is reduced by reducing the size of the window that is sampled. This can be explained with reference back to FIG. 7 and with reference to the high level flow diagram of FIG. 10. Conventionally, as mentioned above, a hemodynamic signal that is to be analyzed would be continuously sampled over multiple cycles of signal. Thus, by only sampling the signal during short windows, the amount of sampling (and number of samples produces) is reduced.

Figure 10:
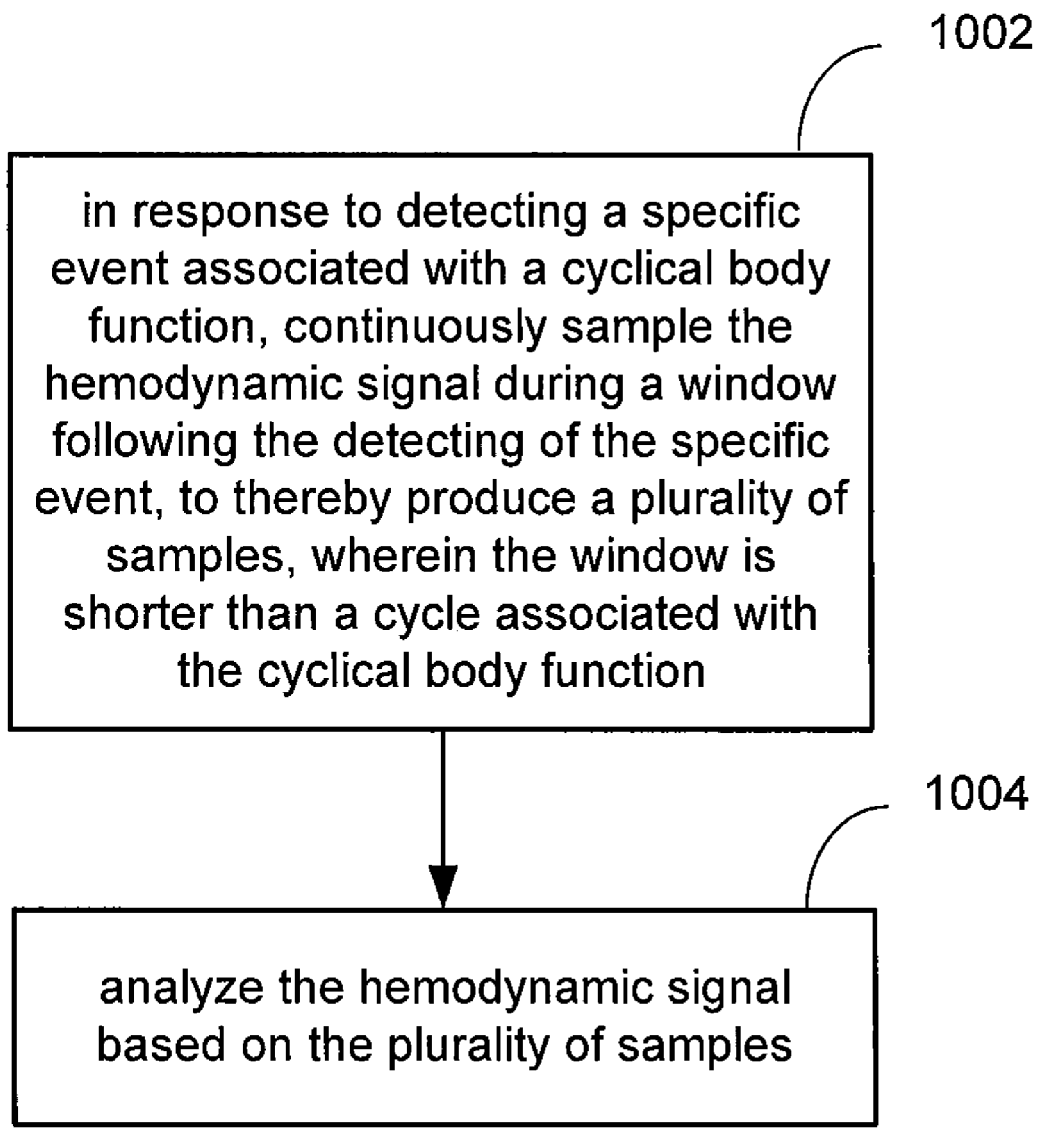
FIG. 10 is a high level flow diagram useful for describing embodiments of the present invention where a hemodynamic signal is continuously sampled during windows following specific events.

Referring to the flow diagram of FIG. 10, at a step 1002, in response to detecting a specific event associated with a cyclical body function, a hemodynamic signal (e.g., a PPG signal or an arterial pressure signal) is continuously sampled during a window following the detecting of a specific event, to thereby produce a plurality of samples. In order to reduce the amount of samples, the window should be shorter than a cycle associated with the cyclical body function. For example, referring back to FIG. 7, the horizontal lines 718 represent windows of time during which the PPG signal 712 is continuously sampled. These windows are clearly shorter than the cardiac cycles shown in the corresponding ECG signal 702, yet they are long enough to include both the onset and completion of the systolic cardiac pulse.

The windows should be wide enough so that the information of interest is captured. For example, if the desire is to obtain the systolic pulse amplitude of a PPG signal during each cardiac cycle, then the window should span the portion of a cycle within which the minimum and maximum are likely to be found. Within a cardiac cycle, the minimum of a corresponding PPG signal will typically occur soon after a ventricular contraction, followed soon after by a maximum of the PPG signal. Accordingly, the window can span, for example, a time beginning with a ventricular contraction and ending a fixed time thereafter. Alternatively, the window can start a fixed delay after a ventricular contraction, or some other specific event. In still other embodiments, the temporal location of the window and the length of the window can be dynamically adjusted to increase the likelihood that the minimum and maximum are sampled, while also minimizing the length of a window.

As with previous embodiments discussed above, the cyclical body function can be heart beat, and the specific event that initiates the sampling can be, for example, sensing a ventricular or atrial contraction, or a ventricular or atrial pace. For those embodiments where the cyclical body function is heart beat, the continuous sampling is preferably performed at a rate of about 20 Hz or greater.

The cyclical body function can alternatively be respiration, and the specific event that initiates the using of the analog circuitry can be expiration or inspiration. Similar to previous embodiments, the window in which sampling is continuously performed can start a fixed delay after a specific event. For those embodiments where the cyclical body function is respiration, the continuous sampling is preferably performed at a rate of about 1 Hz or greater.

Referring back to FIG. 10, at a next step 1004, the hemodynamic signal is analyzed based on the plurality of samples produced at step 1002. For example, step 1004 can include detecting a peak-to-peak amplitude based on the plurality of samples.

In accordance with embodiments of the present invention, step 1002 is repeated a plurality of times such that a plurality of samples is produced for each of a plurality of windows. Then, step 1004 can include averaging the plurality of samples produced for each of the windows to thereby produce an average value for each window. In similar manners as were discussed in detail above, these average values can be used, e.g., for monitoring mean arterial pressure, for pacing interval optimization, and/or for selecting a type of anti-arrhythmia therapy.

Measuring Blood Oxygen Saturation

Embodiments of the present invention are also directed to reducing the amount of processing required to determine a blood oxygen saturation (O2 saturation) level, which is more specifically the percentage of hemoglobin that is saturated with oxygen. Conventionally, measures of arterial O2 saturation are produced using the well-known technique of pulse oximetry in the following way: light of two different wavelengths, typically red (e.g., about 660 nm wavelength) and infrared or near infrared (e.g., about 940 nm wavelength), are alternately transmitted through or reflected by patient tissue such that a single light detector receives incident light that alternates between red and infrared light. More specifically, one LED transmits red light and another LED transmits infrared or near infrared light. The LEDs are serially pulsed to produce an interleaved signal stream that is transmitted through or reflected from tissue of a patient. As the light passes through and/or is reflected from tissue, some of the energy is absorbed by arterial and venous blood, tissue and the variable pulsations of arterial blood. The interleaved red and infrared light stream is received by the single light detector. The amplitudes of the red light pulses in the light stream are differently effected by the absorption than the infrared light pulses, with the absorptions levels depending on the O2 saturation level of the blood.

Using electronic circuitry, firmware and/or software, the received light signals in the infrared and red wavelengths are analyzed so that O2 saturation levels can be determined. At a high level, demultiplexing is used to produce a signal path for the received red light and a separate signal path from the received infrared light. Each signal path will typically include one or more filters and an A/D converter to sample the received light signals. The samples of the red light signal are then used to determine the DC offset (i.e., average) and pulse amplitude of the received red light. Similarly, the samples of the infrared light signal are then used to determine the DC offset (i.e., average) and pulse amplitude of the received infrared light. Each pulse amplitude is then normalized (e.g., by dividing the pulse amplitude by the corresponding DC offset) and a ratio of the red-to-infrared light is determined by dividing the normalized red pulse amplitude by the normalized infrared pulse amplitude. Then, a one dimensional look-up table, such as the exemplary table of FIG. 11A, is typically used to determine the O2 saturation level. A look-up table is typically used because there is a well known one-to-one correspondence between the red-to-infrared ratios and O2 saturation levels. While the just described conventional scheme has worked well, it would be beneficial if the amount of processing required to obtain measures of O2 saturation levels could be reduced. It is noted that for this embodiment and other embodiments described herein it is possible that green light (having a wavelength of about 530 nm) can be used instead of red light.

Using New Look-Up Tables to Determine O2 Saturation

According to embodiments of the present invention, rather than calculating a ratio of red-to-infrared light (by dividing the normalized red pulse amplitude by the normalized infrared pulse amplitude), a two dimensional look-up table is used to determine an O2 saturation level based on a normalized red pulse amplitude and a normalized infrared pulse amplitude. Such a two dimensional look-up table would have normalized red pulse amplitudes along a first axis or dimension, and normalized infrared pulse amplitudes along a second axis or dimension, with the cells of the table populated by corresponding blood oxygenation levels. An example of such a look-up table, according to an embodiment of the present invention, is shown in FIG. 11B. By using a two dimensional look-up table, in accordance with embodiments of the present invention, at least one mathematical division operation is eliminated.

Figure 12:
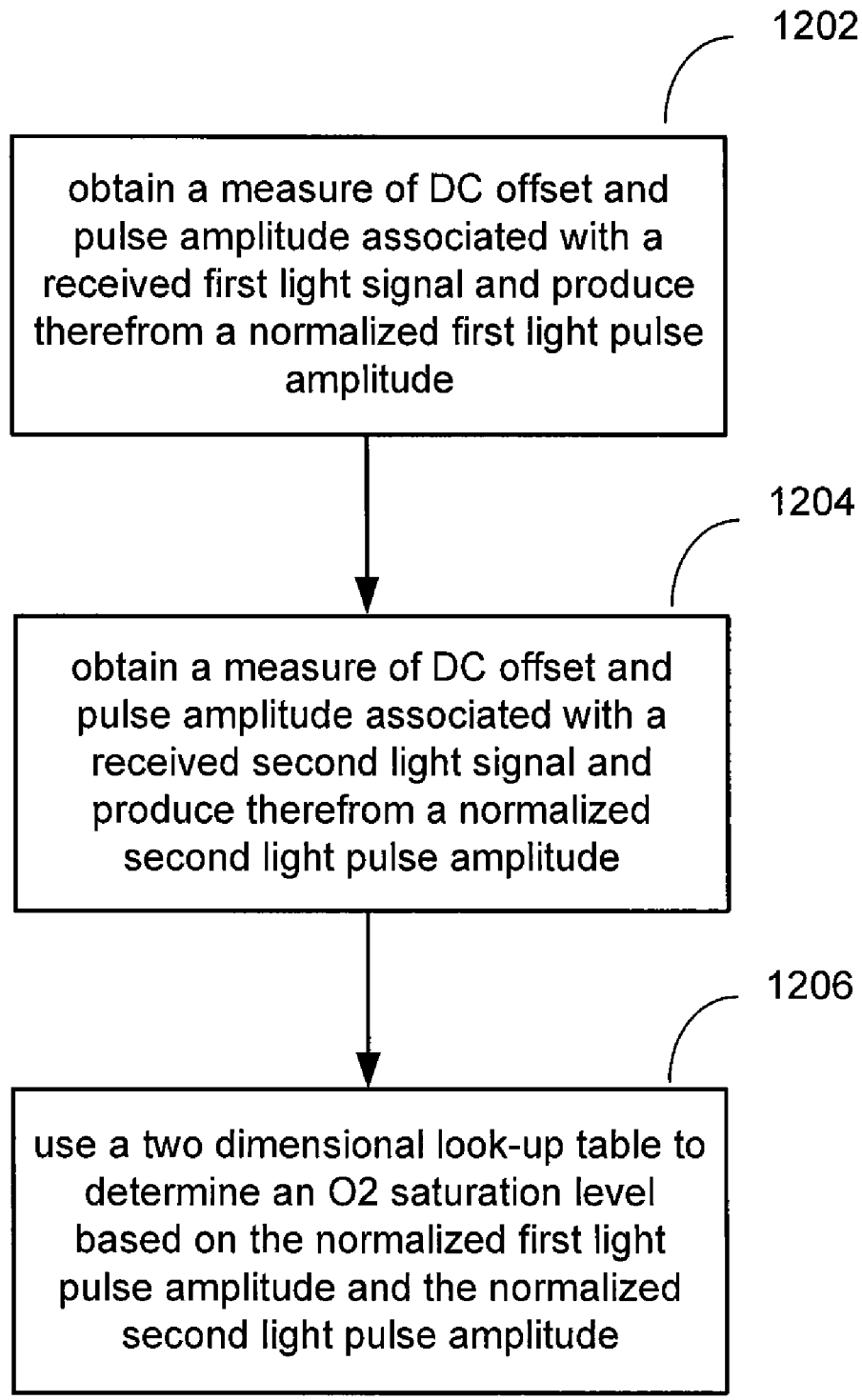
FIG. 12 is a high level flow diagram useful for describing embodiments of the present invention where a two dimensional look-up table, such as the one shown in FIG. 11B, is used to determine oxygen saturation levels.

FIG. 12 is a high level flow diagram useful for describing embodiments of the present invention where a two-dimensional look-up table, such as the one shown in FIG. 11B, is used to determine O2 saturation levels. Referring to FIG. 12, at a step 1202 a measure of DC offset and pulse amplitude associated with a received first light signal is obtained, and a normalized first light pulse amplitude is produced therefrom. The received first light signal can be, e.g., a signal indicative of red light received at a light detector of a pulse oximetry device.

At a step 1204, a measure of DC offset and pulse amplitude associated with a received second light signal is obtained, and a normalized second light pulse amplitude is produced therefrom. The received second light signal can be, e.g., a signal indicative of infrared or near infrared light received at the light detector of the pulse oximetry device.

Then at a step 1206, a two dimensional look-up table (e.g., similar the table of FIG. 11B) is used to determine an O2 saturation level based on the normalized first light pulse amplitude and the normalized second light pulse amplitude.

In accordance with another embodiment of the present invention, a four dimensional look-up table (not shown) is used to determine a blood oxygen saturation level based on non-normalized red and infrared amplitudes and corresponding DC offsets. The four axis or dimensions would include: non-normalized red pulse amplitude, red DC offset, non-normalized infrared pulse amplitude and infrared DC offset. By using a four dimensional look-up table, in accordance with embodiments of the present invention, at least three mathematical division operations are eliminated, as compared to the conventional scheme described above. More specifically, the four dimensional look-up table would be used to determine an O2 saturation level based on obtained measures of DC offset and pulse amplitude associated with a received first light signal, and measures of DC offset and pulse amplitude associated with a received second light signal. The received first light signal can be, e.g., a signal indicative of red light received at a light detector of a pulse oximetry device. The received second light signal can be, e.g., a signal indicative of infrared or near infrared light received at the light detector of the pulse oximetry device.

Simplifying Determinations of DC Offset Used for Measuring O2 Saturation

As was explained above, in order to determine measures of O2 saturation using pulse oximetry, measures of DC offset and pulse amplitude should be obtained for the received red light and infrared light. Typically, to determine the DC offset of each signal, the signal is continuously sampled (prior to any high pass filtering) to produce a plurality of samples from which an average is determined, with the average being the DC offset. The pulse amplitude of each signal is typically determined by high pass filtering the signal to remove the DC offset, and then determining the peak-to-peak amplitude of the signal (or the amplitude above zero). Typically the DC offset and pulse amplitude are measured using separate channels.

In contrast, in accordance with the following embodiments of the present invention, a good estimate of DC offset is obtained from as few as one sample of a DC coupled received light signal (i.e., a signal that has not yet been high pass filtered to remove DC components). More specifically, the magnitude of as few as one sample of a DC coupled received light signal can be determined to provide a good estimate of the DC offset. This is possible because the magnitude of the DC offset is about 100 times larger than the magnitude of the pulse amplitude variations, cardiac variations and respiratory variations (e.g., the DC offset is measured in volts, while the pulse amplitude is measured in millivolts). While as few as one sample could be used to estimate DC offset, it is also possible that a few samples could be averaged to provide a slightly better estimate.

The measures of pulse amplitude can then be obtained in the conventional manner, e.g., by high pass filtering a received light signal and then continuously sampling the high passed filtered signal to determine the amplitude. An improvement here is that the DC offsets of received red and infrared signals are obtained with less sampling, data acquisition, processing and power consumption. In a broad sense, these embodiments can be characterized in that the sampling prior to high pass filtering (for the purposes of estimating DC offset) is at a lower frequency (and possibly a significantly lower frequency) than the sampling frequency used to measure pulse amplitude.

Figure 13:
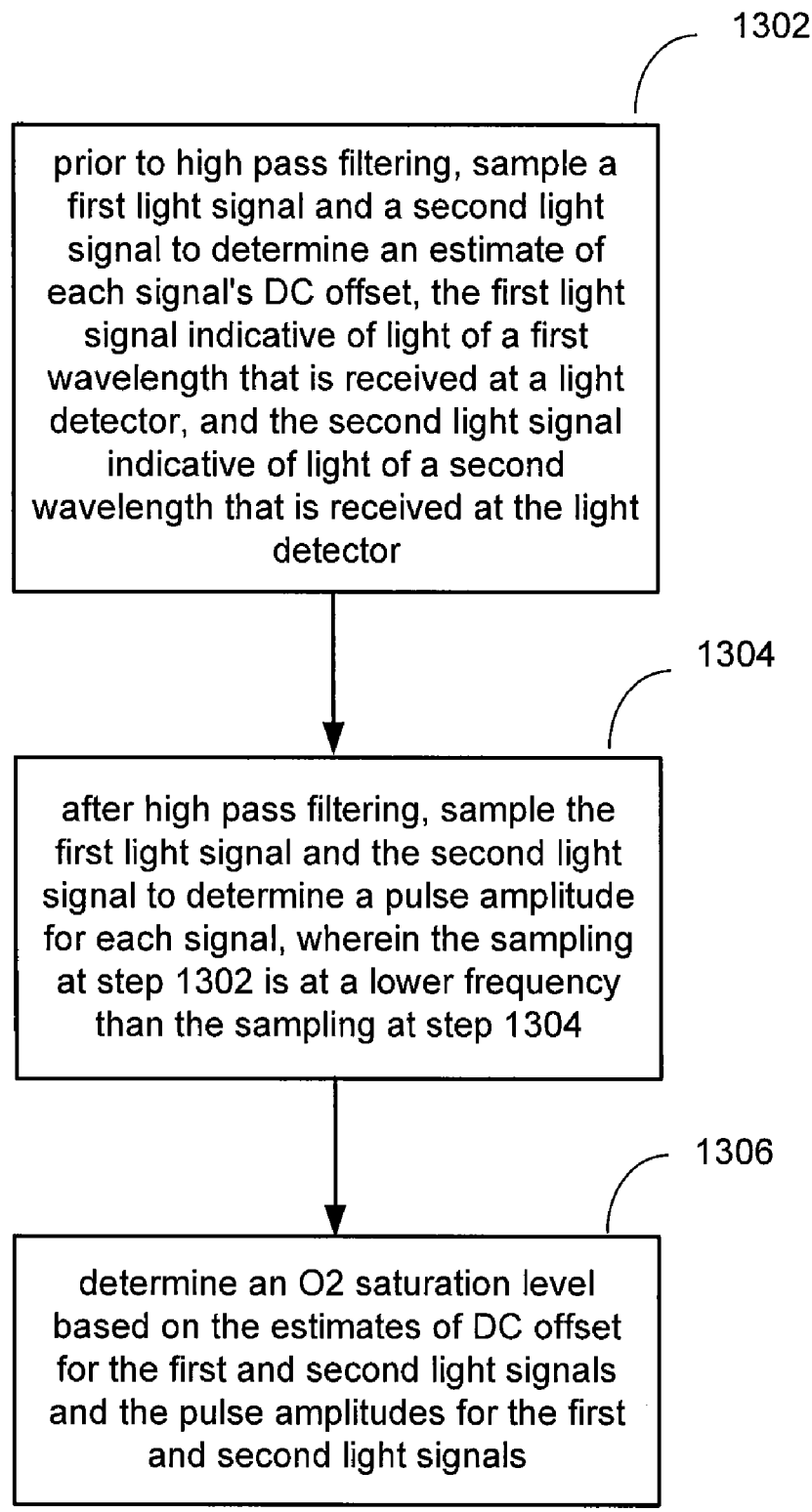
FIG. 13 is a high level flow diagram useful for describing embodiments of the present invention in which lower frequency sampling is used to determine estimates of DC offsets as compared to the frequency of sampling used to determine measures of pulse amplitude.

FIG. 13 will now be used to describe these embodiments of the present invention. Referring to FIG. 13, at a step 1302, prior to high pass filtering, a first light signal and a second light signal are sampled to determine an estimate of each signal's DC offset. The first light signal is indicative of light of a first wavelength (e.g., red or green light) that is received at the light detector. The second light signal is indicative of light of a second wavelength (e.g., infrared or near infrared light) that is received at the light detector. The first light signal can be produced, e.g., by receiving red light at the light detector. The second light signal can be produced, e.g., by receiving infrared or near infrared light at the light detector.

At a step 1304, after high pass filtering, the first light signal and the second light signal are sampled, at a higher frequency than was used at step 1302, to determine a pulse amplitude for each signal. For example, this can be accomplished by continuous sampling the light signals multiple times per cardiac cycle. Alternatively, analog peak detectors can be used, as was described above, and only two samples could be produced per cardiac cycle.

At a step 1306, an O2 saturation level is then determined based on the estimates of DC offset for the first and second light signal and the pulse amplitudes for the first and second light signals. In accordance with an embodiment of the present invention, the frequency of sampling at step 1302 is less than a corresponding cardiac signal frequency, causing the light signals to be sampled once or less per cardiac cycle. In accordance with an embodiment of the present invention, the sampling at step 1302 is a frequency that is at least half of the frequency of the sampling at step 1304, and can even be 100 times less than the frequency used at step 1304.

Adjusting Source Optical Power

Embodiments of the present invention are also directed to adjusting the source optical power such that the light detected at the light detector of a pulse oximetry device has a substantially stable predetermined DC offset. By doing this, the need to perform normalization is eliminated, thereby reducing processing. Such embodiments will be described with reference to the flow diagram of FIG. 14.

Figure 14:
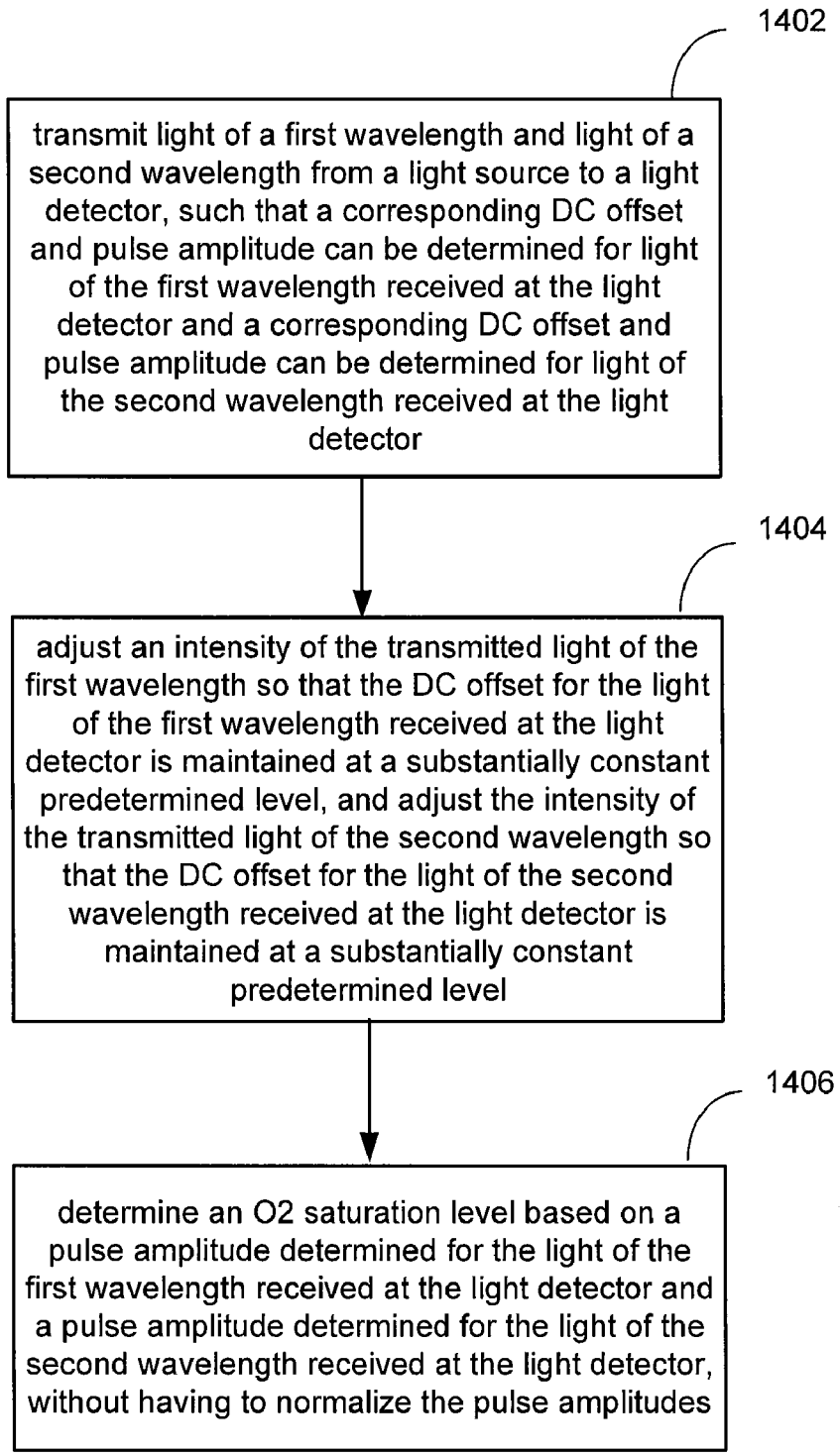
FIG. 14 is a high level flow diagram useful for describing embodiments of the present invention where source optical power is adjusted such that a predetermined DC level is detected at a light detector, thereby eliminating the need to normalize measures of pulse amplitude that are used to determine O2 saturation levels.

Referring to FIG. 14, at a step 1402, light of a first wavelength and light of a second wavelength are transmitted from a light source to a light detector, such that a corresponding DC offset and pulse amplitude can be determined for light of the first wavelength received at the light detector and a corresponding DC offset and pulse amplitude can be determined for light of the second wavelength received at the light detector. The light of the first wavelength can be, e.g., red or green light, and the light of the second wavelength can be, e.g., infrared or near infrared light.

The light source and light detector may be part of a pulse oximetry device, which may or may not be implanted. If implanted, the pulse oximetry device may be part of an implantable monitor or stimulation device that performs other functions beside measuring levels of O2 saturation. It is also possible that such a device uses measures of O2 saturation for various purposes.

At a step 1404, an intensity of the transmitted light of the first wavelength is adjusted so that the DC offset for the light of the first wavelength received at the light detector is maintained at a substantially constant predetermined level. Similarly, the intensity of the transmitted light of the second wavelength is also adjusted so that the DC offset for the light of the second wavelength received at the light detector is maintained at a substantially constant predetermined level. The predetermined level for the light of the first wavelength may or may not be the same of the predetermined level for the light of the second wavelength. This step is most likely accomplished using feedback from the light detector to the light source.

At a step 1406, an O2 saturation level is then determined based on a pulse amplitude determined for the light of the first wavelength received at the light detector and a pulse amplitude determined for the light of the second wavelength received at the light detector. Because this step is performed without having to normalize the pulse amplitudes, processing is reduced.

Exemplary Stimulation Device

Various embodiments discussed above relate to pacing interval optimization, selecting a type of anti-arrhythmia therapy in response to detecting an arrhythmia, sampling a signal in response to detecting a cardiac or respiratory event, etc. For completeness, an exemplary implanted stimulation device 1510 that can be used to perform pacing, detect an arrhythmia, perform anti-arrhythmia therapy, detect specific cardiac events, etc., is described with reference to FIGS. 15A and 15B.

Figure 15A:
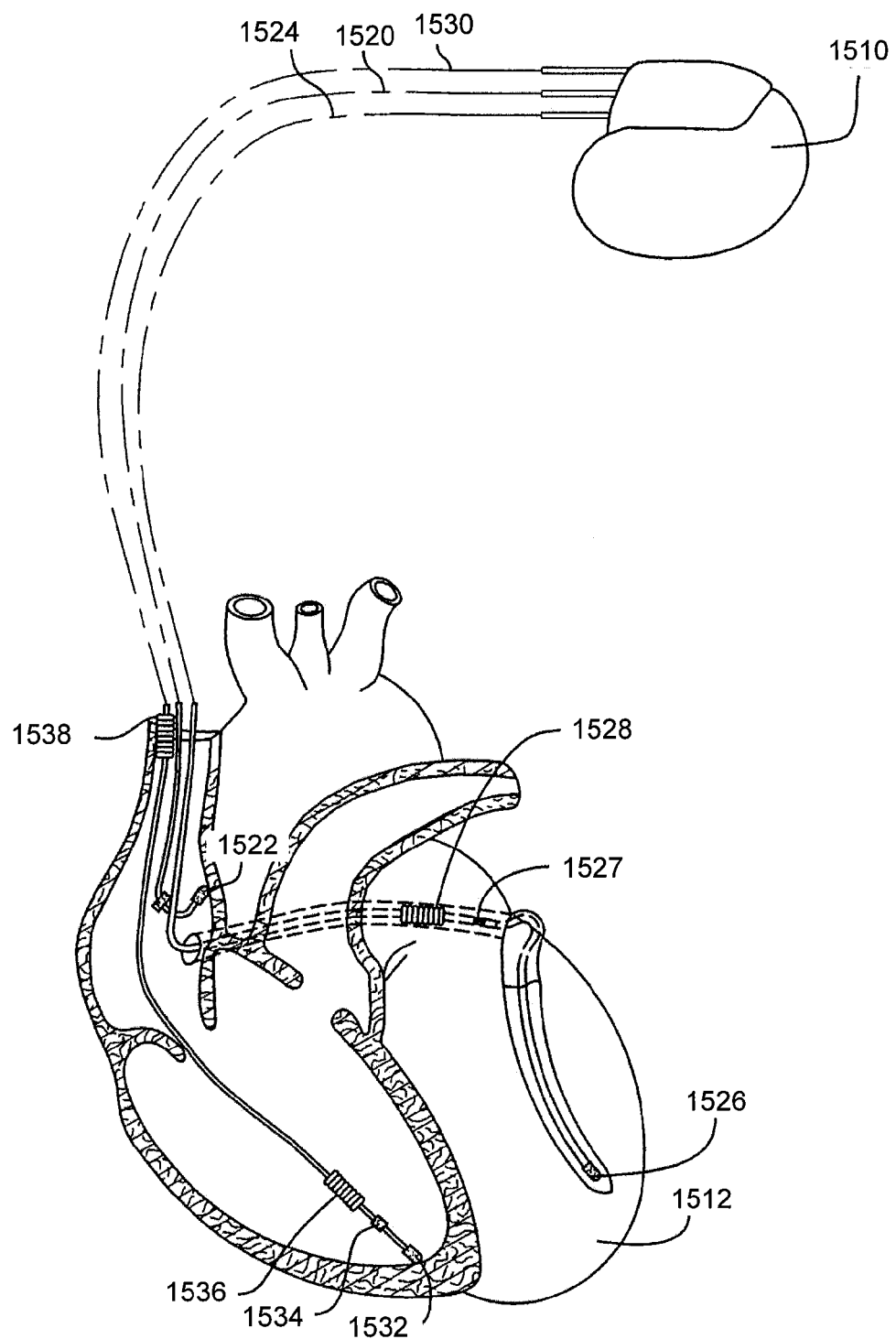
FIG. 15A illustrates an exemplary implantable stimulation device in electrical communication with a patient's heart by way of three leads, which are suitable for delivering multi-chamber stimulation and shock therapy.

Referring to FIG. 15A, the exemplary implantable stimulation device 1510 (also referred to as a pacing device, or a pacing apparatus) is shown as being in electrical communication with a patient's heart 1512 by way of three leads, 1520, 1524 and 1530, suitable for delivering multi-chamber stimulation and shock therapy. To sense atrial cardiac signals and to provide right atrial chamber stimulation therapy, the stimulation device 1510 is coupled to an implantable right atrial lead 1520 having at least an atrial tip electrode 1522, which typically is implanted in the patient's right atrial appendage. Stimulation device 1510 can be integrated with one of the embodiments of the monitor 500 discussed above. That is, a common housing can be used to contain the elements of the monitor 500 (e.g., a light source 206 and light detector 214) and the elements of the stimulation device 1510. More generally, the sensor that produces an arterial plethysmography signal can be in the same housing that contains the stimulation device. Alternatively, separates housings can be used to house the monitor 500 and the stimulation device 1510. This is of course necessary if a monitor in not implantable (e.g., in embodiments where the one or more sensors associated with a monitor are incorporated into a finger cuff, a wristband, a configuration resembling a watch, or a configuration resembling a clip-on earring). As mentioned above, the sensor that produces the arterial plethysmography signal can be a PPG sensor. Alternatively, a strain gauge, a linear displacement sensor, or ultrasound transducer can be used.

Referring to FIG. 15A, to sense left atrial and ventricular cardiac signals and to provide left-chamber pacing therapy, the stimulation device 1510 is coupled to a "coronary sinus" lead 1524 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

A pressure transducer can be located on the right atrial lead 1520, on lead 1530, or on an a separate lead (now shown), to enable the device 1510 to produce a right atrial, right ventricular, or arterial pulse pressure hemodynamic signal, respectively. Alternatively, pressure transducers can be placed from right heart leads transeptally into the left atrium or even the left ventricle in order obtain left atrial and left ventricular pressures. It is also possible that a hollow lumen catheter can be inserted in an artery or within a heart chamber, with the hollow lumen catheter being in communication with a pressure transducer located within the device housing 1540. These approaches to pressure sensing can be used in a chronically implanted device, or can be placed temporarily to allow acute measurements, as during diagnostic or therapeutic maneuvers or for monitoring in intensive care settings.

The exemplary coronary sinus lead 1524 is designed to receive atrial and ventricular cardiac signals and to deliver left ventricular pacing therapy using at least a left ventricular tip electrode 1526, left atrial pacing therapy using at least a left atrial ring electrode 1527, and shocking therapy using at least a left atrial coil electrode 1528.

The stimulation device 1510 is also shown in electrical communication with the patient's heart 1512 by way of an implantable right ventricular lead 1530 having, in this embodiment, a right ventricular tip electrode 1532, a right ventricular ring electrode 1534, a right ventricular (RV) coil electrode 1536, and an SVC coil electrode 1538. Typically, the right ventricular lead 1530 is transvenously inserted into the heart 1512 so as to place the right ventricular tip electrode 1532 in the right ventricular apex so that the RV coil electrode 1536 will be positioned in the right ventricle and the SVC coil electrode 1538 will be positioned in the superior vena cava. Accordingly, the right ventricular lead 1530 is capable of receiving cardiac signals and delivering stimulation in the form of pacing and shock therapy to the right ventricle.

Figure 15B:
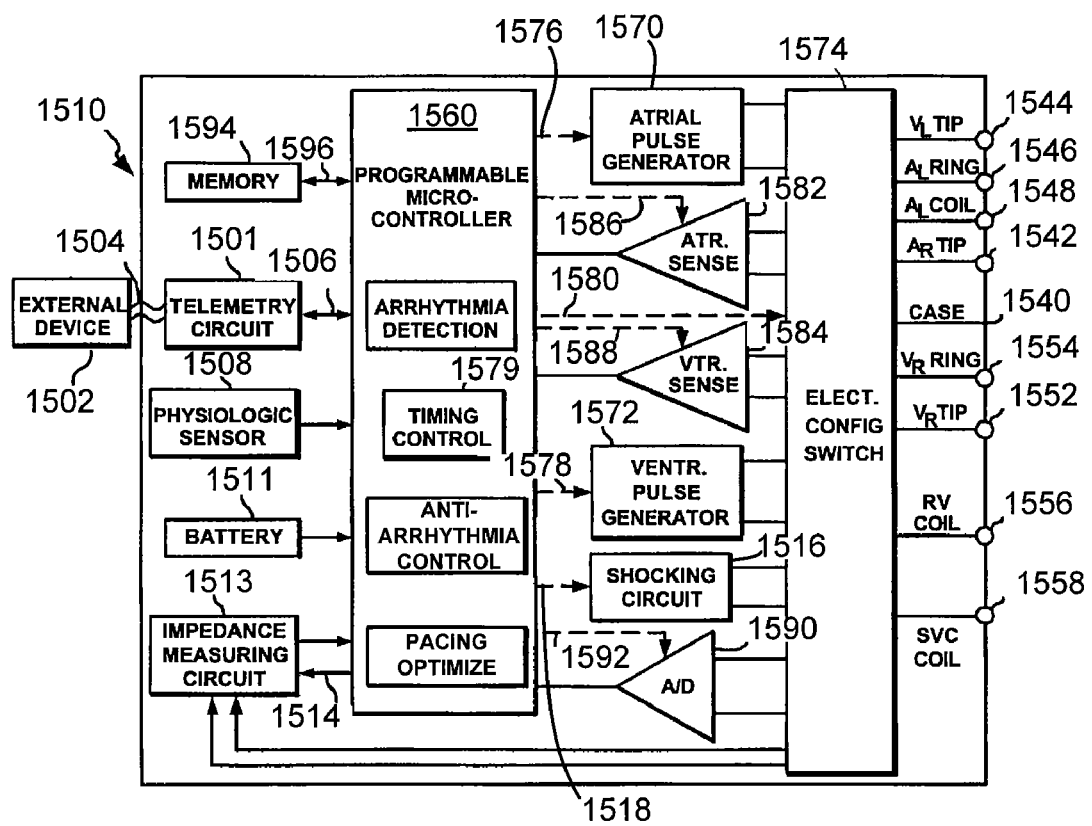
FIG. 15B is a simplified block diagram of the multi-chamber implantable stimulation device of FIG. 15A.

As illustrated in FIG. 15B, a simplified block diagram is shown of the multi-chamber implantable stimulation device 1510, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 1540 for the stimulation device 1510, shown schematically in FIG. 15B, is often referred to as the "can", "case" or "case electrode" and may be programmably selected to act as the return electrode for all "unipolar" modes. The housing 1540 may further be used as a return electrode alone or in combination with one or more of the coil electrodes, 1528, 1536 and 1538, for shocking purposes. The housing 1540 further includes a connector (not shown) having a plurality of terminals, 1542, 1544, 1546, 1548, 1552, 1554, 1556, and 1558 (shown schematically and, for convenience, the names of the electrodes to which they are connected are shown next to the terminals). As such, to achieve right atrial sensing and pacing, the connector includes at least a right atrial tip terminal ($A_R$ TIP) 1542 adapted for connection to the atrial tip electrode 1522.

To achieve left chamber sensing, pacing and shocking, the connector includes at least a left ventricular tip terminal ($V_L$ TIP) 1544, a left atrial ring terminal ($A_L$ RING) 1546, and a left atrial shocking terminal ($A_L$ COIL) 48, which are adapted for connection to the left ventricular ring electrode 1526, the left atrial tip electrode 1527, and the left atrial coil electrode 1528, respectively.

To support right chamber sensing, pacing and shocking, the connector further includes a right ventricular tip terminal ($V_R$ TIP) 1552, a right ventricular ring terminal ($V_R$ RING)

1554, a right ventricular shocking terminal (R$_V$ COIL) 1556, and an SVC shocking terminal (SVC COIL) 1558, which are adapted for connection to the right ventricular tip electrode 1532, right ventricular ring electrode 1534, the RV coil electrode 1536, and the SVC coil electrode 1538, respectively. At the core of the stimulation device 1510 is a programmable microcontroller 1560 which controls the various modes of stimulation therapy, including pacing optimization and anti-arrhythmia therapy. As is well known in the art, the microcontroller 1560 typically includes a microprocessor, or equivalent control circuitry, designed specifically for controlling the delivery of stimulation therapy and can further include RAM or ROM memory, logic and timing circuitry, state machine circuitry, and I/O circuitry. Typically, the microcontroller 1560 includes the ability to analyze signals (data) as controlled by a program code stored in a designated block of memory. The details of the design of the microcontroller 1560 are not critical to the present invention. Rather, any suitable microcontroller 1560 can be used to carry out the functions described herein. The use of microprocessor-based control circuits for performing timing and data analysis functions are well known in the art. In specific embodiment of the present invention, the microcontroller 1560 performs some or all of the steps associated with detecting specific events, triggering sampling, monitoring mean arterial pressure, pacing interval optimization and selecting an appropriate anti-arrhythmia therapy. It is noted that the microcontroller 1560 and microprocessor 530 can be one in the same, or separate, depending on implementation and embodiment.

Representative types of control circuitry that may be used with the invention include the microprocessor-based control system of U.S. Pat. No. 4,940,052 (Mann et. al.) and the state-machines of U.S. Pat. No. 4,712,555 (Sholder) and U.S. Pat. No. 4,944,298 (Sholder). For a more detailed description of the various timing intervals used within the stimulation device and their inter-relationship, see U.S. Pat. No. 4,788,980 (Mann et. al.). The '052, '555, '298 and '980 patents are incorporated herein by reference.

As shown in FIG. 15B, an atrial pulse generator 1570 and a ventricular pulse generator 1572 generate pacing stimulation pulses for delivery by the right atrial lead 1520, the right ventricular lead 1530, and/or the coronary sinus lead 1524 via an electrode configuration switch 1574. It is understood that in order to provide stimulation therapy in each of the four chambers of the heart, the atrial and ventricular pulse generators, 1570 and 1572, may include dedicated, independent pulse generators, multiplexed pulse generators, or shared pulse generators. The pulse generators, 1570 and 1572, are controlled by the microcontroller 1560 via appropriate control signals, 1576 and 1578, respectively, to trigger or inhibit the stimulation pulses.

The microcontroller 1560 further includes timing control circuitry 1579 which is used to control pacing parameters (e.g., the timing of stimulation pulses) as well as to keep track of the timing of refractory periods, PVARP intervals, noise detection windows, evoked response windows, alert intervals, marker channel timing, etc., which is well known in the art. Examples of pacing parameters include, but are not limited to, atrio-ventricular delay, interventricular delay and interatrial delay.

The switch bank 1574 includes a plurality of switches for connecting the desired electrodes to the appropriate I/O circuits, thereby providing complete electrode programmability. Accordingly, the switch 1574, in response to a control signal 1580 from the microcontroller 1560, determines the polarity of the stimulation pulses (e.g., unipolar, bipolar, combipolar, etc.) by selectively closing the appropriate combination of switches (not shown) as is known in the art.

Atrial sensing circuits 1582 and ventricular sensing circuits 1584 may also be selectively coupled to the right atrial lead 1520, coronary sinus lead 1524, and the right ventricular lead 1530, through the switch 1574 for detecting the presence of cardiac activity in each of the four chambers of the heart. Accordingly, the atrial (ATR. SENSE) and ventricular (VTR. SENSE) sensing circuits, 1582 and 1584, may include dedicated sense amplifiers, multiplexed amplifiers, or shared amplifiers. The switch 1574 determines the "sensing polarity" of the cardiac signal by selectively closing the appropriate switches, as is also known in the art. In this way, the clinician may program the sensing polarity independent of the stimulation polarity.

Each sensing circuit, 1582 and 1584, preferably employs one or more low power, precision amplifiers with programmable gain and/or automatic gain control, bandpass filtering, and a threshold detection circuit, as known in the art, to selectively sense the cardiac signal of interest. The automatic gain control enables the device 1510 to deal effectively with the difficult problem of sensing the low amplitude signal characteristics of atrial or ventricular fibrillation. Such sensing circuits, 1582 and 1584, can be used to determine cardiac performance values used in the present invention.

The outputs of the atrial and ventricular sensing circuits, 1582 and 1584, are connected to the microcontroller 1560 which, in turn, are able to trigger or inhibit the atrial and ventricular pulse generators, 1570 and 1572, respectively, in a demand fashion in response to the absence or presence of cardiac activity, in the appropriate chambers of the heart. The sensing circuits, 1582 and 1584, in turn, receive control signals over signal lines, 1586 and 1588, from the microcontroller 1560 for purposes of measuring cardiac performance at appropriate times, and for controlling the gain, threshold, polarization charge removal circuitry (not shown), and timing of any blocking circuitry (not shown) coupled to the inputs of the sensing circuits, 1582 and 1586.

For arrhythmia detection, the device 1510 utilizes the atrial and ventricular sensing circuits, 1582 and 1584, to sense cardiac signals to determine whether a rhythm is physiologic or pathologic. The timing intervals between sensed events (e.g., P-waves, R-waves, and depolarization signals associated with fibrillation which are sometimes referred to as "F-waves" or "Fib-waves") are then classified by the microcontroller 1560 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to assist with determining the type of remedial therapy that is needed (e.g., bradycardia pacing, anti-tachy-cardia pacing, cardioversion shocks or defibrillation shocks, collectively referred to as "tiered therapy").

Cardiac signals are also applied to the inputs of an analog-to-digital (A/D) data acquisition system 1590. The data acquisition system 1590 is configured to acquire intracardiac electrogram signals, convert the raw analog data into a digital signal, and store the digital signals for later processing and/or telemetric transmission to an external device 1502. The data acquisition system 1590 is coupled to the right atrial lead 1520, the coronary sinus lead 1524, and the right ventricular lead 1530 through the switch 1574 to sample cardiac signals across any pair of desired electrodes.

Advantageously, the data acquisition system 1590 can be coupled to the microcontroller 1560, or other detection circuitry, for detecting an evoked response from the heart 1512 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 1560 detects a depolarization signal during a window following a stimulation pulse, the presence of which indicates that capture has occurred. The microcontroller 1560 enables capture detection by triggering the ventricular pulse generator 1572 to generate a stimulation pulse, starting a capture detection window using the timing control circuitry 1579 within the microcontroller 1560, and enabling the data acquisition system 1590 via control signal 1592 to sample the cardiac signal that falls in the capture detection window and, based on the amplitude, determines if capture has occurred.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et. al.); and U.S. Pat. No. 5,350,410 (Mann et. al.), which patents are hereby incorporated herein by reference. The type of capture detection system used is not critical to the present invention.

The microcontroller 1560 is further coupled to a memory 1594 by a suitable data/address bus 1596, wherein the programmable operating parameters used by the microcontroller 1560 are stored and modified, as required, in order to customize the operation of the stimulation device 1510 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 1512 within each respective tier of therapy.

A feature of the present invention is the ability to sense and store data (e.g., from the data acquisition system 1590). Such data can then be used for subsequent analysis to guide the programming of the device and/or to monitor mean arterial pressure, appropriately adjust pacing interval parameters, select optimum pacing intervals, and/or select appropriate anti-arrhythmia therapy, in accordance with embodiments of the present invention.

Advantageously, the operating parameters of the implantable device 1510 may be non-invasively programmed into the memory 1594 through a telemetry circuit 1501 in telemetric communication with the external device 1502, such as a programmer, transtelephonic transceiver, or a diagnostic system analyzer. The telemetry circuit 1501 is activated by the microcontroller by a control signal 1506. The telemetry circuit 1501 advantageously allows intracardiac electrograms and status information relating to the operation of the device 1510 (as contained in the microcontroller 1560 or memory 1594) to be sent to an external device 1502 through an established communication link 1504.

For examples of such devices, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. patent application Ser. No. 09/223,422, filed Dec. 30, 1998, entitled "Efficient Generation of Sensing Signals in an Implantable Medical Device such as a Pacemaker or ICD" (note: this relates to transfer of EGM data) (McClure et al.), which patents are hereby incorporated herein by reference.

In accordance with an embodiment, the stimulation device 1510 further includes one or more physiologic sensors 1508, that can be used, e.g., to produce an arterial plethysmography signal. The physiologic sensors 1508 can include, for example, a PPG sensor having light source and a light detector (e.g., similar to light source 206 and light detector 214). In other words, portions of the PPG sensor, described in detail above, can be incorporated into or with the stimulation device 1510. This would enable the stimulation device 1510 to produce an arterial plethysmography signal that is useful for monitoring the mean arterial pressure of the patient and obtaining data for pulse oximetry calculations, and to produce a venous plethysmography signal that is useful for monitoring respiration. The microcontroller 1560 can respond by selecting and/or adjusting the various pacing parameters (e.g., atrio-ventricular delay, interventricular delay, interatrial delay etc.), based on measures of mean arterial pressure determined using the plethysmography signal. As explained above, other types of sensors can alternatively be used to produce an arterial plethysmography signal.

The microcontroller 1560 can respond to changes in mean arterial pressure by adjusting the various pacing parameters in accordance with the embodiments of the present invention. The microcontroller 1560 controls adjustments of pacing parameters by, for example, controlling the stimulation pulses generated by the atrial and ventricular pulse generators, 1570 and 1572. While shown as being included within the stimulation device 1510, it is to be understood that the physiologic sensor 1508 may also be external to the stimulation device 1510, yet still be implanted within or carried by the patient. More specifically, the sensor 1508 can be located inside the device 1510, on the surface of the device 1510, in a header of the device 1510, or on a lead (which can be placed inside or outside the bloodstream).

The stimulation device 1510 additionally includes a battery 1511 which provides operating power to all of the circuits shown in FIG. 15B. For the stimulation device 1510, which employs shocking therapy, the battery 1511 must be capable of operating at low current drains for long periods of time, and then be capable of providing high-current pulses (for capacitor charging) when the patient requires a shock pulse. The battery 1511 must also have a predictable discharge characteristic so that elective replacement time can be detected. Accordingly, the device 1510 preferably employs lithium/silver vanadium oxide batteries, as is true for most (if not all) current devices.

The stimulation device 1510 further includes a magnet detection circuitry (not shown), coupled to the microcontroller 1560. It is the purpose of the magnet detection circuitry to detect when a magnet is placed over the stimulation device 1510, which magnet may be used by a clinician to perform various test functions of the stimulation device 10 and/or to signal the microcontroller 1560 that the external programmer 1502 is in place to receive or transmit data to the microcontroller 1560 through the telemetry circuits 100.

As further shown in FIG. 15B, the device 1510 is shown as having an impedance measuring circuit 1513 which is enabled by the microcontroller 1560 via a control signal 1514. The known uses for an impedance measuring circuit 1513 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; measuring thoracic impedance for detecting and assessing the severity of pulmonary edema; detecting when the device has been implanted; measuring stroke volume; and detecting the opening of heart valves, etc. The impedance measuring circuit 1513 is advantageously coupled to the switch 1574 so that any desired electrode may be used. In addition, to facilitate the measurement of peripheral tissue edema, extra electrodes can be added to the device housing, thereby limiting the test electric field to the peripheral tissue.

In the case where the stimulation device 1510 is also intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 1560 further controls a shocking circuit 1516 by way of a control signal 1518. The shocking circuit 1516 generates shocking pulses of low (up to 0.5 Joules), moderate (0.5-10 Joules), or high energy (11 to 40 Joules), as controlled by the microcontroller 1560. Such shocking pulses are applied to the patient's heart 1512 through at least two shocking electrodes, and as shown in this embodiment, selected from the left atrial coil electrode 1528, the RV coil electrode 1536, and/or the SVC coil electrode 1538. As noted above, the housing 1540 may act as an active electrode in combination with the RV electrode 1536, or as part of a split electrical vector using the SVC coil electrode 1538 or the left atrial coil electrode 1528 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 Joules), delivered asynchronously (since R-waves may be too disorganized to be recognize), and pertaining exclusively to the treatment of fibrillation. Accordingly, the microcontroller 1560 is capable of controlling the synchronous or asynchronous delivery of the shocking pulses. Another approach to electrical anti-arrhythmia therapy is anti-tachycardia pacing, in which low-voltage pacing pulses are applied to pace-terminate the arrhythmia. This approach is particularly effective in low rate ventricular tachycardias.

CONCLUSION

The previous description of the preferred embodiments is provided to enable any person skilled in the art to make or use the embodiments of the present invention. While the invention has been particularly shown and described with reference to preferred embodiments thereof, it will be understood by those skilled in the art that various changes in form and details may be made therein without departing from the spirit and scope of the invention.

What is claimed is:

1. A method for reducing the amount of data required to analyze a hemodynamic signal, comprising:
   (a) for a window of time that spans at least two respiratory cycles, producing only one sample of the hemodynamic signal per respiratory cycle, at a substantially same instant in each respiratory cycle, to thereby produce a plurality of samples for the window; and
   (b) analyzing the hemodynamic signal based on the plurality of samples,
   wherein each said sample is indicative of an amplitude of the hemodynamic signal at a single moment in one of the respiratory cycles.

2. The method of claim 1, wherein step (a) comprises sampling the hemodynamic signal in response to a specific respiratory event.

3. The method of claim 2, wherein the sampling of the hemodynamic signal in step (a) occurs a fixed delay after the specific respiratory event.

4. The method of claim 1, wherein step (a) comprises sampling the hemodynamic signal in response to one of the following respiratory events:
   expiration; and
   inspiration.

5. The method of claim 4, wherein the sampling of the hemodynamic signal in step (a) occurs a fixed delay after the specific respiratory event.

6. A method for reducing the amount of data required to analyze a hemodynamic signal, comprising:
   (a) for each of a plurality of windows of time, producing only one sample of the hemodynamic signal per respiratory cycle, at a substantially same instant in each respiratory cycle, to thereby produce a plurality of samples for each window, wherein each window spans at least two respiratory cycles;
   (b) for each of the plurality of windows, averaging the plurality of samples, to thereby produce an average value for each window; and
   (c) analyzing the hemodynamic signal based on the average values,
   wherein each said sample is indicative of an amplitude of the hemodynamic signal at a single moment in one of the respiratory cycles.

7. The method of claim 6, wherein step (a) comprises sampling the hemodynamic signal in response to a specific respiratory event.

8. The method of claim 7, wherein the sampling of the hemodynamic signal in step (a) occurs a fixed delay after the specific respiratory event.

9. The method of claim 6, wherein step (a) comprises sampling the hemodynamic signal in response to one of the following respiratory events:
   expiration; and
   inspiration.

10. The method of claim 9, wherein the sampling of the hemodynamic signal in step (a) occurs a fixed delay after the specific respiratory event.

11. A method for reducing the amount of data required to analyze a photoplethysmography (PPG) hemodynamic signal, comprising:
    (a) for each of a plurality of windows of time, producing only one sample of the PPG signal per respiratory cycle, at a substantially same instant in each respiratory cycle, to thereby produce a plurality of samples for each window, wherein each window spans at least two respiratory cycles, and wherein each said sample is indicative of an amplitude of the PPG signal at a single moment in one of the respiratory cycles;
    (b) for each of the plurality of windows, averaging the plurality of samples, to thereby produce an average value for each window; and
    (c) analyzing the PPG signal based on the average values.

12. The method of claim 11, wherein the PPG signal is produced using a device that is not implanted in a patient.

13. The method of claim 11, wherein the PPG signal is produced using a device that is implanted in a patient.

14. The method of claim 13, wherein the PPG signal is produced using a light source and a light detector that are implanted in the patient.

15. The method of claim 11, wherein the PPG signal is produced by:
    transmitting light from a light source;
    receiving, at a light detector, a portion of the light transmitted from the light source; and
    producing the PPG signal based on the received portion of light.

16. The method of claim 11, wherein the PPG signal is produced using a light source and a light detector, and wherein the light source is only pulsed once per respiratory cycle, thereby reducing power consumption.

17. The method claim 11, wherein the window of the PPG signal spans one of the following:

a predetermined time interval;

a predetermined number of cardiac cycles; and a predetermined number of respiratory cycles.

18. The method of claim 11, wherein in step (a), during the sampling of the PPG signal only once per respiratory cycle, the respiratory cycles that are sampled within each window need not be consecutive respiratory cycles.

* * * * *